United States Patent
Liu et al.

(10) Patent No.: US 9,593,373 B2
(45) Date of Patent: Mar. 14, 2017

(54) MODIFIED NUCLEOSIDES OR NUCLEOTIDES

(71) Applicant: Illumina Cambridge Limited, Nr Saffron Walden, Essex (GB)

(72) Inventors: Xiaohai Liu, Nr Saffron Walden (GB); Xiaolin Wu, Nr Saffron Walden (GB); Geoffrey Paul Smith, Nr Saffron Walden (GB)

(73) Assignee: Illumina Cambridge Limited, Essex (GB)

( * ) Notice: Subject to any disclaimer, the term of this patent is extended or adjusted under 35 U.S.C. 154(b) by 0 days.

(21) Appl. No.: 14/771,481

(22) PCT Filed: Mar. 15, 2013

(86) PCT No.: PCT/EP2013/055466
§ 371 (c)(1),
(2) Date: Aug. 28, 2015

(87) PCT Pub. No.: WO2014/139596
PCT Pub. Date: Sep. 18, 2014

(65) Prior Publication Data
US 2016/0002721 A1    Jan. 7, 2016

(51) Int. Cl.
| | |
|---|---|
| C12Q 1/68 | (2006.01) |
| C07H 21/04 | (2006.01) |
| C07H 19/073 | (2006.01) |
| C07H 19/10 | (2006.01) |
| C07H 19/14 | (2006.01) |
| C07H 19/173 | (2006.01) |
| C07H 19/20 | (2006.01) |

(52) U.S. Cl.
CPC ......... *C12Q 1/6869* (2013.01); *C07H 19/073* (2013.01); *C07H 19/10* (2013.01); *C07H 19/14* (2013.01); *C07H 19/173* (2013.01); *C07H 19/20* (2013.01); *C12Q 1/6876* (2013.01); *Y02P 20/55* (2015.11)

(58) Field of Classification Search
CPC ............................ C12Q 1/6869; C07H 19/073
USPC ............................ 536/4.1, 23.1; 435/6.1, 91.1
See application file for complete search history.

(56) References Cited

U.S. PATENT DOCUMENTS

| | | |
|---|---|---|
| 4,772,691 A | 9/1988 | Herman |
| 4,888,274 A | 12/1989 | Radding et al. |
| 5,047,519 A | 9/1991 | Hobbs, Jr. et al. |

(Continued)

FOREIGN PATENT DOCUMENTS

| | | |
|---|---|---|
| WO | WO 89/10977 | 11/1989 |
| WO | WO 91/06678 | 5/1991 |

(Continued)

OTHER PUBLICATIONS

International Search Report and Written Opinion for Application No. PCT/EP2013/055466, mailed Oct. 29, 2013.

(Continued)

*Primary Examiner* — Jezia Riley
(74) *Attorney, Agent, or Firm* — Knobbes Martens Olson & Bear LLP

(57) ABSTRACT

Some embodiments described herein relate to modified nucleotide and nucleoside molecules with novel 3'-hydroxy protecting groups. Also provided herein are methods to prepare such modified nucleotide and nucleoside molecules and sequencing by synthesis processes using such modified nucleotide and nucleoside molecules.

20 Claims, 4 Drawing Sheets

(56) References Cited

U.S. PATENT DOCUMENTS

| | | | |
|---|---|---|---|
| 5,242,796 | A | 9/1993 | Prober et al. |
| 5,302,509 | A | 4/1994 | Cheeseman |
| 5,547,839 | A | 8/1996 | Dower et al. |
| 5,602,000 | A | 2/1997 | Hyman |
| 5,635,400 | A | 6/1997 | Brenner |
| 5,798,210 | A | 8/1998 | Canard et al. |
| 5,959,089 | A | 9/1999 | Hannessian |
| 6,001,566 | A | 12/1999 | Canard et al. |
| 6,013,445 | A | 1/2000 | Albrecht |
| 6,087,112 | A | 7/2000 | Dale |
| 6,221,592 | B1 | 4/2001 | Schwartz et al. |
| 6,255,083 | B1 | 7/2001 | Williams |
| 6,432,360 | B1 | 8/2002 | Church |
| 6,664,079 | B2 | 12/2003 | Ju et al. |
| 6,818,395 | B1 | 11/2004 | Quake et al. |
| 7,057,026 | B2 | 6/2006 | Barnes et al. |
| 7,078,499 | B2 | 7/2006 | Odedra et al. |
| 7,223,540 | B2 | 5/2007 | Pourmand et al. |
| 7,270,951 | B1 | 9/2007 | Stemple et al. |
| 7,279,563 | B2 | 10/2007 | Kwiatkowski |
| 7,393,533 | B1 | 7/2008 | Crotty et al. |
| 7,713,698 | B2 | 5/2010 | Ju et al. |
| 7,785,790 | B1 | 8/2010 | Church et al. |
| 8,158,346 | B2 | 4/2012 | Balasubramanian et al. |
| 2003/0104437 | A1 | 6/2003 | Barnes et al. |
| 2003/0180769 | A1 | 9/2003 | Metzker |
| 2006/0160081 | A1 | 7/2006 | Milton et al. |
| 2010/0159531 | A1 | 6/2010 | Gordon |
| 2010/0323350 | A1 | 12/2010 | Gordon |
| 2011/0124054 | A1 | 5/2011 | Olejnik |
| 2012/0052489 | A1 | 3/2012 | Gordon |

FOREIGN PATENT DOCUMENTS

| | | |
|---|---|---|
| WO | WO 93/21340 | 10/1993 |
| WO | WO 96/23807 | 8/1996 |
| WO | WO 96/27025 | 9/1996 |
| WO | WO 98/33939 | 8/1998 |
| WO | WO 99/49082 | 9/1999 |
| WO | WO 00/53805 | 9/2000 |
| WO | WO 00/53812 | 9/2000 |
| WO | WO 01/92284 | 12/2001 |
| WO | WO 02/29003 | 4/2002 |
| WO | WO 03/048387 | 6/2003 |
| WO | WO 2004/018493 | 3/2004 |
| WO | WO 2004/018497 | 3/2004 |
| WO | WO 2004/018497 A2 | 3/2004 |
| WO | WO 2009/054922 A1 | 4/2009 |
| WO | WO 2012/083249 A2 | 6/2012 |
| WO | WO 2012/162429 A2 | 11/2012 |

OTHER PUBLICATIONS

Aldrich Chemical Company, Fine Chemicals, 1986 Edition, p. 1337.
Bebenek K. et al., Frameshift errors initiated by nucleotide misincorporation, PNAS USA, 87: 4946-4950 (1990).
Bebenek K. et al., The Effects of dNTP Pool Imbalances on Frameshift Fidelity during DNA Replication, J. Biol. Chem., 267: 3589-3596 (1992).
Beckman Coulter CEQ™ 2000—DNA Analysis System—User's Guide, Jun. 2000, 234 pages.
Bentley D.R. et al., Accurate whole human genome sequencing using reversible terminator chemistry, Nature, 2008, 456: 53-59.
Bi L. et al., Design and Synthesis of a Chemically Cleavable Fluorescent Nucleotide,3'-O-Allyl-dGTP-allyl-Bodipy-FL-510, as a Reversible Terminator for DNA Sequencing by Synthesis, J. Am. Chem. Soc., 2006, 128: 2542-2543.
Brown T. et al., "Modern machine-aided methods of oligodeoxyribonucleotide synthesis," pp. 1-11; and Ruth J.L., "Oligodeoxynucleotides with reporter groups attached to the base," p. 255, in *Oligonucleotides and Analogues, A Practical Approach*, ed. Eckstein, Oxford Univ. Press, New York (1991).
Burgess K. et al., An Approach to Photolabile, Fluorescent Protecting Groups, J. Org. Chem. 1997, 62: 5165-5168.
Burns J.A. et al., Selective Reduction of Disulfides by Tris(2-carboxyethyl)phosphine, J. Org. Chem., 56: 2648-2650 (1991).
Bystrom C.E. et al., ATP Analogs with non-transferable groups in the gamma-position as inhibitors of glycerol kinase, Bioorg Med Chem Letts. 7: 2613-2616 (1997).
Canard B. et al., DNA polymerase fluorescent substrates with reversible 3'-tags, Gene, 1994, 148: 1-6.
Canard B. et al., Catalytic editing properties of DNA polymerases , Proc. Natl. Acad. Sci. USA, 1995, 92: 10859-10863.
Christensen L. F. et al., Specific Chemical Synthesis of Ribonucleoside O-Benzyl Ethers , J. Org. Chem., 1972, 37(22): 3398-3401.
Dantas F.J.S. et al., Stannous chloride mediates single strand breaks in plasmid DNA through reactive oxygen species formation, Toxicology Letters, 1999, 110:.129-136.
Dawson B.A. et al., Affinity Isolation of Transcriptionally Active Murine Erythroleukemia Cell DNA Using a Cleavable Biotinylated Nucleotide Analog, J Biol. Chem., 264(22): 12830-12837 (1989).
Dawson B. A. et al., Affinity Isolation of Active Murine Erythroleukemia Cell Chromatin: Uniform Distribution of Ubiquitinated Histone H2A between Active and Inactive Fractions, J Cell Biochem. 46: 166-173 (1991).
Fersht A.R., Fidelity of replication of phage Øx174 DNA by DNA polymerase III holoenzyme: Spontaneous mutation by misincorporation, PNAS USA, 76: 4946-4950 (1979).
Fersht A.R. et al., DNA polymerase accuracy and spontaneous mutation rates: Frequencies of purine-purine, purine-pyrimidine, and pyrimidine-pyrimidine mismatches during DNA replication, PNAS USA, 78: 4251-4255 (1981).
Gardner A.F. et al., Determinants of nucleotide sugar recognition in an archaeon DNA polymerase, Nucleic Acids Research, 1999, 27(12): 2545-2553.
Greene et al., The Role of Protective Groups in Organic Synthesis, *Protective Groups in Organic Synthesis*, $3^{RD}$Edition (1999), John Wiley & Sons, Inc. Chapter 1, pp. 20.
Greene et al., Protection for Phenols and Catechols, *Protective Groups in Organic Synthesis*, $3^{RD}$Edition (1999), John Wiley & Sons, Inc. Chapter 3, pp. 246-292.
Greene et al., *Protective Groups in Organic Synthesis*, $3^{RD}$ Edition (1999), John Wiley & Sons, Inc.—Excerpts; pp. 316.
Guo et al., Four-color DNA sequencing with 3'-O-modified nucleotide reversible terminators and chemically cleavable fluorescent dideoxynucleotides, PNAS, 2008, 105: 9145-9150.
Guo J., Thesis: Molecular Engineering of Novel Nucleotide Analogues for DNA Sequencing and Analysis, Columbia University, 2009, 206 pages.
Handlon A.L. et al., Thiol Reduction of 3'-Azidothymidine to 3'-Aminothymidine: Kinetics and Biomedical Implications, Pharm. Res. 5(5): 297-99 (1988).
Hanlon S., The Importance of London Dispersion Forces in the Maintenance of the Deoxyribonucleic Acid Helix, Biochemical and Biophysical Research Communications, 1966, 23(6): 861-867.
Holtzman E. et. al., Electron microscopy of complexes of isolated acetylcholine receptor, biotinyltoxin, and avidin, PNAS USA, 79: 310-314 (1982).
Iyer R.P. et al., Nucleoside Oxazaphospholidines as Novel Synthons in Oligonucleotide Synthesis, J. Org. Chem., 1995, 60: 5388-5389.
Ju J. et al., Four-color DNA sequencing by synthesis using cleavable fluorescent nucleotide reversible terminators, PNAS, 2006, 103(52): 19635-19640.
Jung M.E. et al., Conversion of Alkyl Carbamates into Amines via Treatment with Trimethylsilyl Iodide, J.C.S. Chem. Comm. (7):315-316, 1978.
Kamal A. et al., A Mild and Rapid Regeneration of Alcohols from their Allylic Ethers by Chlorotrimethylsilane/Sodium Iodide, Tetrahed. Letts 40(2): 371-372, 1999.
Katagiri N. et al., "Selective Protection of the Primary Hydroxyl Groups of Oxetanocin A and Conformational Analysis of O-protected Oxetanocin A", Chem. Pharm. Bull. 43(5): 884-886 (1995).

(56) References Cited

OTHER PUBLICATIONS

Kim D. H., Thesis: Four-Color DNA Sequencing by Synthesis on a Chip Using Cleavable Fluorescent Nucleotide Reversible Terminators, Columbia University, 2008, 216 pages.
Kit S., Deoxyribonucleic Acids, Annu. Rev. Biochem., 1963, 32: 43-82.
Klausner A., Dupont's DNA Sequencer uses new chemistry, Nat. Biotech. 5: 1111-1112 (1987).
Kraevskii A.A. et al., Substrate Inhibitors of DNA Biosynthesis, (translated from Russian) Molecular Biology, 1987, 21(1): 25-29.
Lee C.-H. et al., Unwinding of double-stranded DNA helix by dehydration, Proc. Natl. Acad. Sci. USA, 1981, 78(5): 2838-2842.
Letsinger R.L. et al., 2,4-Dinitrobenzenesulfenyl as a Blocking Group for Hydroxyl Functions in Nucleosides, J. Org. Chem. 29: 2615-2618 (1964).
Loubinoux B. et al., Protection of Phenols by the Azidomethylene Group Application to the Synthesis of Unstable Phenols, (English Translation from French) Tetrahedron 1988, 44(19): 6055-6064; 18 pages.
Lukesh J.C. et al., A Potent, Versatile Disulfide-Reducing Agent from Aspartic Acid, J. Am. Chem. Soc., 134: 4057-59 (2012).
Mardis E.R., A decade's perspective on DNA sequencing technology, Nature, 2011, 470: 198-203.
Maxam A.M. et al., A new method for sequencing DNA, PNAS USA, 1977, 74(2): 560-564.
Meng Q. et al., Design and Synthesis of a Photocleavable Fluorescent Nucleotide 3'-O-Allyl-dGTP-PC-Bodipy-FL-510 as a Reversible Terminator for DNA Sequencing by Synthesis , J. Org. Chem., 2006, 71: 3248-3252.
Meng Q., Thesis: Part I. Tandem Aldol-allylation Reactions Promoted by Strained Silacycles. Part II. Design and Synthesis of Modified Fluorescent Nucleotides for DNA Sequencing by Synthesis, Columbia University, 2006, 303 pages.
Merck Index, The, Entry for Phenol, an Encyclopedia of Chemicals, Drugs, and Biologicals, 2001, 13th Ed., pp. 1299-1300.
Merck Index, The, Entry for Triphenylphosphine, an Encyclopedia of Chemicals, Drugs, and Biologicals, 2001, 13th Ed., p. 1735.
Metzker M.L. et al., Termination of DNA synthesis by novel 3'-modified-deoxyribonucleoside 5'-triphosphates, Nucleic Acids Research, 1994, 22(20): 4259-4267.
Metzker M.L., Emerging technologies in DNA sequencing, Genome Research, 2005, 15: 1767-1776.
Metzker M.L., Sequencing Technologies—The Next Generation, Nature Reviews Genetics, 2010, 11: 31-46.
Mitra R.D. et al., Fluorescent in situ sequencing on polymerase colonies, Anal Biochem. 320: 55-65 (2003).
Mullis K.B. et al., "Specific Synthesis of DNA in Vitro via a Polymerase-Catalyzed Chain Reaction," pp. 335-350, in Methods in Enzymology, vol. 155, Recombinant DNA, Part F, ed. Wu, Academic Press, Inc., San Diego (1987).
Mungall W.S. et al., Use of the Azido Group in the Synthesis of 5' Terminal Aminodeoxythymidine Oligonucleotides, J. Org. Chem., (1975) 40(11):1659-1662.
Murakami K. et al., Structure of a *Plasmodium yoelii* gene-encoded protein homologous to the ca$^{2+}$-ATPase of rabbit skeletal muscle sarcoplasmic reticulum, J. Cell Sci., 97: 487-495 (1990).
Mussini T. et al., Criteria for standardization of pH measurements in organic solvents and water + organic solvent mixtures of moderate to high permittivities, Pure & Appl. Chem., 1985, 57(6): 865-876.
Pierce Chemical Company—1999/2000 Products Catalog, (1999) 48 pages.
Pilard S. et al., A stereospecific synthesis of (±) α-conhydrine and (±) β-conhydrine, Tetrahedron Letts, 1984, 25(15): 1555-1556.
Prober J.M. et al., A System for Rapid DNA Sequencing with Fluorescent Chain-Terminating Dideoxynucleotides, Science, 1987, 238: 336-341.
Pugliese L. et al., Three-dimensional Structure of the Tetragonal Crystal Form of Egg-white Avidin in its Functional Complex with Biotin at 2-7 Å Resolution, J Mol Biol. 231: 698-710 (1993).
Qui C., Thesis: Novel Molecular Engineering Approaches for Genotyping and DNA Sequencing, Columbia University, 2011; 282 pages.
Ranganathan R. et al., Facile Conversion of Adenosine Into New 2'-Substituted-2'-Deoxy-Arabinofuranosyladenine Derivatives : Stereospecific Synthesis of 2'-Azido-2'-Deoxy-,2'-Amino-Z'-Deoxy-, and 2'-Mercapto-2'-Deoxy-BD-Arabinofuranosyladenine, Tetra. Letts. 1978, 45: 4341-4344.
Rigas B. et al., Rapid plasmid library screening using RecA-coated biotinylated probes, PNAS USA 83: 9591-9595 (1986).
Ruby S.W. et al., Affinity Chromatography with Biotinylated RNAs, Meth Enzymol. 1990, 181: 97-121.
Ruparel H. et al., Design and synthesis of a 3-O-allyl photocleavable fluorescent nucleotide as a reversible terminator for DNA sequencing by synthesis, PNAS, 2005, 102: 5932-5938.
Sanger F. et al., DNA sequencing with chain-terminating inhibitors, PNAS USA, 1977, 74(12): 5463-5467.
Shen L.X. et al., RNA structure at high resolution, FASEB J., 9: 1023-1033 (1995).
Shendure J. et al., Advanced Sequencing Technologies: Methods and Goals, Nature Reviews Genetics, 2004, 5: 335-345.
Taylor P. et al., Rise per base pair in helices of double-stranded rotavirus RNA determined by electron microsopy, Virus Research, 2: 175-182 (1985).
Tietze L.F. et al., Synthesis of a Novel Stable GM$_3$-Lactone Analogue as Hapten for a Possible Immunization against Cancer, Angew. Chem. Int. Ed. Engl., 1997, 36(15): 1615-1617.
Treinin A., General and Theoretical Aspects, The Chemistry of the Azido Group, Saul Patai, Ed., 1971, Chapter 1, pp. 1-55.
Tsai S.-C. et al., Versatile and Efficient Synthesis of a New Class of Aza-Based Phosphinic Amide Ligands via Unusual P—C Cleavage, Helvetica Chimica Acta, 2006, 89: 3007-3017.
Watkins B.E. et al., Synthesis of Oligodeoxyribonucleotides Using N-Benzyloxycarbonyl-Blocked Nucleosides, J. Am. Chem. Soc., 1982, 104: 5702-5708.
Watson J.D. et al., [Eds.] The Structures of DNA and RNA, in *Molecular Biology of the Gene*, 5$^{th}$ Edition, Chapter 6 (2004), 34 pages.
Welch M.B. et al., Syntheses of Nucleosides Designed for Combinatorial DNA Sequencing, Chem. Eur. J. 1999, 5(3): 951-960.
Welch M.B. et al., Synthesis of fluorescent, photolabile 3'-O-protected nucleoside triphosphates for the base addition sequencing scheme, Nucleosides Nucleotides, 1999, 18(2): 197-201.
Welch M. et al., Corrigenda: Synthesis of Nucleosides Designed for Combinatorial DNA Sequencing, Chem. Eur. J., 11: 7145 (2005).
Westheimer F.H., Why Nature Chose Phosphates, Science 235:1173-1178 (1987).
Wu J. et al., 3'-O-modified nucleotides as reversible terminators for pyrosequencing, PNAS, 2007, 104: 16462-16467.
Wu J., Thesis: Molecular Engineering of Novel Nucleotide Analogues for DNA Sequencing by Synthesis, Columbia University, 2008, 231 pages.
Yoshimoto K. et al., Tris(2,4,6-trimethoxyphenyl)phosphine (TTMPP): A Novel Catalyst for Selective Deacetylation, Chem Letts., 2001, 30: 934-935.
Yu L., Thesis: Novel Strategies to Increase Read Length and Accuracy for DNA Sequencing by Synthesis, Columbia University, 2010, 196 pages.
Zavgorodny S. et al., 1-Alkylthioalkylation of Nucleoside Hydroxyl Functions and Its Synthetic Applications: A New Versatile Method in Nucleoside Chemistry, Tetrahedron Letts. 32(51): 7593-7596 (1991).
Zhang S., Thesis: Development of New DNA Sequencing Approaches and Investigation of Vision-related Proteins Using Synthetic Chemistry, Columbia University, 2008, 319 pages.
Petition for Inter Partes Review of U.S. Pat. No. 7,057,026 dated Feb. 7, 2013.
Final Written Decision of the PTAB regarding Inter Partes Review of U.S. Pat. No. 7,057,026 dated Jul. 25, 2014.
Petition for Inter Partes Review of U.S. Pat. No. 7,566,537 dated Aug. 30, 2013.

(56) References Cited

OTHER PUBLICATIONS

Final Written Decision of the PTAB regarding Inter Partes Review of U.S. Pat. No. 7,566,537 dated Feb. 11, 2015.
Petition for Inter Partes Review of U.S. Pat. No. 8,158,346 dated May 4, 2013.
Final Written Decision of the PTAB regarding Inter Partes Review of U.S. Pat. No. 8,158,346 dated Oct. 28, 2014.

MODIFIED NUCLEOSIDES OR NUCLEOTIDES

CROSS-REFERENCE TO RELATED APPLICATIONS

The present application is the U.S. National Phase under 35 U.S.C. §371 of International Application No. PCT/EP2013/055466, entitled "MODIFIED NUCLEOSIDES OR NUCLEOTIDES," filed Mar. 15, 2013, and published in English on Sep. 18, 2014 as WO2014/139596 A1.

BACKGROUND

Field of the Invention

Some embodiments described herein relate to modified nucleotides or nucleosides comprising 3'-hydroxy protecting groups and their use in polynucleotide sequencing methods. Some embodiments described herein relate to method of preparing the 3'-hydroxy protected nucleotides or nucleosides.

Description of the Related Art

Advances in the study of molecules have been led, in part, by improvement in technologies used to characterize the molecules or their biological reactions. In particular, the study of the nucleic acids DNA and RNA has benefited from developing technologies used for sequence analysis and the study of hybridization events.

An example of the technologies that have improved the study of nucleic acids is the development of fabricated arrays of immobilized nucleic acids. These arrays consist typically of a high-density matrix of polynucleotides immobilized onto a solid support material. See, e.g., Fodor et al., *Trends Biotech.* 12: 19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci.* 92: 6379-6383, 1995).

One way of determining the nucleotide sequence of a nucleic acid bound to an array is called "sequencing by synthesis" or "SBS". This technique for determining the sequence of DNA ideally requires the controlled (i.e., one at a time) incorporation of the correct complementary nucleotide opposite the nucleic acid being sequenced. This allows for accurate sequencing by adding nucleotides in multiple cycles as each nucleotide residue is sequenced one at a time, thus preventing an uncontrolled series of incorporations occurring. The incorporated nucleotide is read using an appropriate label attached thereto before removal of the label moiety and the subsequent next round of sequencing.

In order to ensure only a single incorporation occurs, a structural modification ("protecting group") is added to each labeled nucleotide that is added to the growing chain to ensure that only one nucleotide is incorporated. After the nucleotide with the protecting group has been added, the protecting group is then removed, under reaction conditions which do not interfere with the integrity of the DNA being sequenced. The sequencing cycle can then continue with the incorporation of the next protected, labeled nucleotide.

To be useful in DNA sequencing, nucleotides, and more usually nucleotide triphosphates, generally require a 3'-hydroxy protecting group so as to prevent the polymerase used to incorporate it into a polynucleotide chain from continuing to replicate once the base on the nucleotide is added. There are many limitations on types of groups that can be added onto a nucleotide and still be suitable. The protecting group should prevent additional nucleotide molecules from being added to the polynucleotide chain whilst simultaneously being easily removable from the sugar moiety without causing damage to the polynucleotide chain. Furthermore, the modified nucleotide needs to be tolerated by the polymerase or other appropriate enzyme used to incorporate it into the polynucleotide chain. The ideal protecting group therefore exhibits long term stability, be efficiently incorporated by the polymerase enzyme, cause blocking of secondary or further nucleotide incorporation and have the ability to be removed under mild conditions that do not cause damage to the polynucleotide structure, preferably under aqueous conditions.

Reversible protecting groups have been described previously. For example, Metzker et al., (*Nucleic Acids Research*, 22 (20): 4259-4267, 1994) discloses the synthesis and use of eight 3'-modified 2-deoxyribonucleoside 5'-triphosphates (3'-modified dNTPs) and testing in two DNA template assays for incorporation activity. WO 2002/029003 describes a sequencing method which may include the use of an allyl protecting group to cap the 3'-OH group on a growing strand of DNA in a polymerase reaction.

In addition, we previously reported the development of a number of reversible protecting groups and methods of deprotecting them under DNA compatible conditions in International Application Publication No. WO 2004/018497, which is hereby incorporated by reference in its entirety.

SUMMARY

Some embodiments described herein relate to a modified nucleotide or nucleoside molecule comprising a purine or pyrimidine base and a ribose or deoxyribose sugar moiety having a removable 3'-hydroxy protecting group forming a structure —O—C(R)$_2$N$_3$ covalently attached to the 3'-carbon atom, wherein R is selected from the group consisting of hydrogen, —C(R$^1$)$_m$(R$^2$)$_n$, —C(=O)OR$^3$, —C(=O)NR$^4$R$^5$, —C(R$^6$)$_2$O(CH$_2$)$_p$NR$^7$R$^8$ and —C(R$^9$)$_2$O-Ph-C(=O)NR$^{10}$R$^{11}$;

each R$^1$ and R$^2$ is independently selected from hydrogen, optionally substituted alkyl or halogen;

R$^3$ is selected from hydrogen or optionally substituted alkyl;

each R$^4$ and R$^5$ is independently selected from hydrogen, optionally substituted alkyl, optionally substituted aryl, optionally substituted heteroaryl, or optionally substituted aralkyl;

each R$^6$ and R$^9$ is selected from hydrogen, optionally substituted alkyl or halogen;

each R$^7$, R$^8$, R$^{10}$ and R$^{11}$ is independently selected from hydrogen, optionally substituted alkyl, optionally substituted aryl, optionally substituted heteroaryl, or optionally substituted aralkyl;

m is an integer of 0 to 3; and n is an integer of 0 to 3; provided that the total of m+n equals to 3; and p is an integer of 0 to 6; provided that R$^1$ and R$^2$ cannot both be halogen; and at least one R is not hydrogen.

Some embodiments described herein relate to a method of preparing a growing polynucleotide complementary to a target single-stranded polynucleotide in a sequencing reaction, comprising incorporating a modified nucleotide molecule described herein into the growing complementary polynucleotide, wherein the incorporation of the modified nucleotide prevents the introduction of any subsequent nucleotide into the growing complementary polynucleotide.

Some embodiments described herein relate to a method for determining the sequence of a target single-stranded polynucleotide, comprising monitoring the sequential incorporation of complementary nucleotides, wherein at least one complementary nucleotide incorporated is a modified nucleotide molecule described herein; and detecting the identity of the modified nucleotide molecule. In some embodiments, the incorporation of the modified nucleotide molecule is accomplished by a terminal transferase, a terminal polymerase or a reverse transcriptase.

Some embodiments described herein relate to a kit comprising a plurality of modified nucleotide or nucleoside molecule described herein, and packaging materials therefor. In some embodiments, the identity of the modified nucleotide is determined by detecting the detectable label linked to the base. In some such embodiments, the 3'-hydroxy protecting group and the detectable label are removed prior to introducing the next complementary nucleotide. In some such embodiments, the 3'-hydroxy protecting group and the detectable label are removed in a single step of chemical reaction.

DETAILED DESCRIPTION

Figure 1A:
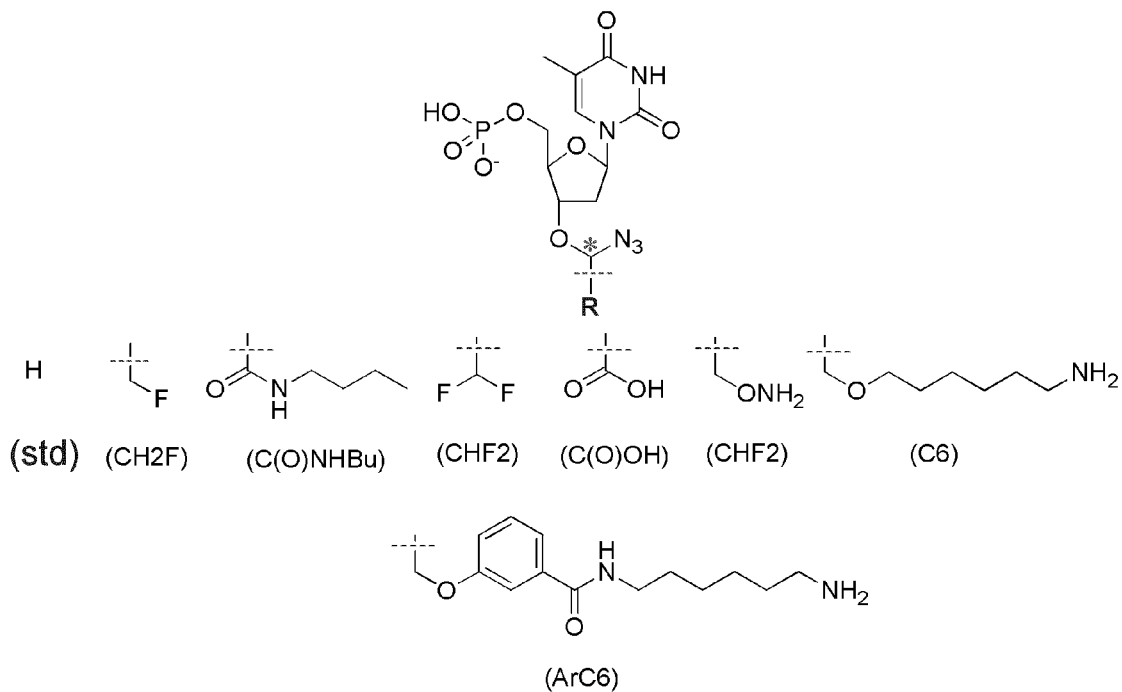
FIG. 1A illustrates a variety of 3'-OH protecting groups.

One embodiment is a modified nucleotide or nucleoside comprising a 3'-OH protecting group. In one embodiment, the 3'-OH protecting group is a monofluoromethyl substituted azidomethyl protecting group. In another embodiment, the 3'-OH protecting group is a C-amido substituted azidomethyl protecting group. Still another embodiment relates to modified nucleotides having difluoromethyl substituted azidomethyl 3'-OH protecting groups.

Definitions

Unless defined otherwise, all technical and scientific terms used herein have the same meaning as is commonly understood by one of ordinary skill in the art. The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

As used herein, common organic abbreviations are defined as follows:

Ac Acetyl
$Ac_2O$ Acetic anhydride
aq. Aqueous
Bn Benzyl
Bz Benzoyl
BOC or Boc tert-Butoxycarbonyl
Bu n-Butyl
cat. Catalytic
Cbz Carbobenzyloxy
° C. Temperature in degrees Centigrade
dATP Deoxyadenosine triphosphate
dCTP Deoxycytidine triphosphate
dGTP Deoxyguanosine triphosphate
dTTP Deoxythymidine triphosphate
ddNTP(s) Dideoxynucleotide(s)
DBU 1,8-Diazabicyclo[5.4.0]undec-7-ene
DCA Dichloroacetic acid
DCE 1,2-Dichloroethane
DCM Methylene chloride
DIEA Diisopropylethylamine
DMA Dimethylacetamide
DME Dimethoxyethane
DMF N,N'-Dimethylformamide
DMSO Dimethylsulfoxide
DPPA Diphenylphosphoryl azide
Et Ethyl
EtOAc Ethyl acetate
ffN Fully functional nucleotide
g Gram(s)
GPC Gel permeation chromatography
h or hr Hour(s)
iPr Isopropyl
KPi 10 mM potassium phosphate buffer at pH 7.0
KPS Potassium persulfate
IPA Isopropyl Alcohol
IMX Incorporation mix
LCMS Liquid chromatography-mass spectrometry
LDA Lithium diisopropylamide
m or min Minute(s)
mCPBA meta-Chloroperoxybenzoic Acid
MeOH Methanol
MeCN Acetonitrile
Mono-F —$CH_2F$
Mono-F ffN modified nucleotides with —$CH_2F$ substituted on methylene position of azidomethyl 3-OH protecting group
mL Milliliter(s)
MTBE Methyl tertiary-butyl ether
$NaN_3$ Sodium Azide
NHS N-hydroxysuccinimide
PG Protecting group
Ph Phenyl
ppt Precipitate
rt Room temperature
SBS Sequencing by Synthesis
TEA Triethylamine
TEMPO (2,2,6,6-Tetramethylpiperidin-1-yl)oxyl
TCDI 1,1'-Thiocarbonyl diimidazole
Tert, t tertiary TFA Trifluoracetic acid
THF Tetrahydrofuran
TEMED Tetramethylethylenediamine
μL Microliter(s)

As used herein, the term "array" refers to a population of different probe molecules that are attached to one or more substrates such that the different probe molecules can be differentiated from each other according to relative location. An array can include different probe molecules that are each located at a different addressable location on a substrate. Alternatively or additionally, an array can include separate substrates each bearing a different probe molecule, wherein the different probe molecules can be identified according to the locations of the substrates on a surface to which the substrates are attached or according to the locations of the substrates in a liquid. Exemplary arrays in which separate substrates are located on a surface include, without limitation, those including beads in wells as described, for example, in U.S. Pat. No. 6,355,431 B1, US 2002/0102578 and PCT Publication No. WO 00/63437. Exemplary formats that can be used in the invention to distinguish beads in a liquid array, for example, using a microfluidic device, such as a fluorescent activated cell sorter (FACS), are described, for example, in U.S. Pat. No. 6,524,793. Further examples of arrays that can be used in the invention include, without limitation, those described in U.S. Pat. Nos. 5,429,807; 5,436,327; 5,561,071; 5,583,211; 5,658,734; 5,837,858; 5,874,219; 5,919,523; 6,136,269; 6,287,768; 6,287,776; 6,288,220; 6,297,006; 6,291,193; 6,346,413; 6,416,949; 6,482,591; 6,514,751 and 6,610,482; and WO 93/17126; WO 95/11995; WO 95/35505; EP 742 287; and EP 799 897.

As used herein, the term "covalently attached" or "covalently bonded" refers to the forming of a chemical bonding that is characterized by the sharing of pairs of electrons between atoms. For example, a covalently attached polymer coating refers to a polymer coating that forms chemical bonds with a functionalized surface of a substrate, as compared to attachment to the surface via other means, for example, adhesion or electrostatic interaction. It will be appreciated that polymers that are attached covalently to a surface can also be bonded via means in addition to covalent attachment.

As used herein, any "R" group(s) such as, without limitation, $R^2$, $R^3$, $R^4$, $R^5$, $R^6$, $R^7$, and $R^8$ represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring, an example of which is set forth below:

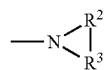

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from a group of functionalies including, but not limited to, alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group, di-substituted amino group, and protected derivatives thereof.

As used herein, "alkyl" refers to a straight or branched hydrocarbon chain that comprises a fully saturated (no double or triple bonds) hydrocarbon group. In some embodiments, the alkyl group may have 1 to 20 carbon atoms (whenever it appears herein, a numerical range such as "1 to 20" refers to each integer in the given range inclusive of the endpoints; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having about 7 to about 10 carbon atoms. The alkyl group can also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). In some embodiments, cycloalkyl groups can contain 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, in some embodiments, the aryl group can be a $C_6$-$C_{14}$ aryl group, a $C_6$-$C_{10}$ aryl group, or a $C_6$ aryl group.

Examples of aryl groups include, but are not limited to, benzene, naphthalene, and azulene. An aryl group may be substituted or unsubstituted.

As used herein, "heterocyclyl" refers to ring systems including at least one heteroatom (e.g., O, N, S). Such systems can be unsaturated, can include some unsaturation, or can contain some aromatic portion, or be all aromatic. A heterocyclyl group may be unsubstituted or substituted.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, in some embodiments, a heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "heteroalicyclic" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heteroalicyclic may be quaternized. Heteroalicyclyl or heteroalicyclic groups may be unsubstituted or substituted. Examples of such "heteroalicyclic" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

As used herein, "alkoxy" refers to the formula —OR wherein R is an alkyl, an alkenyl, an alkynyl, a cycloalkyl, a cycloalkenyl or a cycloalkynyl is defined as above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, a "C-amido" group refers to a "—C(=O)N($R_a R_b$)" group in which $R_a$ and $R_b$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. A C-amido may be substituted or unsubstituted.

As used herein, an "N-amido" group refers to a "RC(=O)N($R_a$)—" group in which R and $R_a$ can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An N-amido may be substituted or unsubstituted.

The term "halogen atom", "halogen" or "halo" as used herein, means any one of the radio-stable atoms of column 7 of the Periodic Table of the Elements, such as, fluorine, chlorine, bromine, and iodine.

The term "amine" as used herein refers to a —$NH_2$ group wherein one or more hydrogen can be optionally substituted by a R group. R can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl) alkyl.

The term "aldehyde" as used herein refers to a —$R_c$—C(O)H group, wherein $R_c$ can be absent or independently selected from alkylene, alkenylene, alkynylene, cycloalkylene, cycloalkenylene, cycloalkynylene, arylene, heteroarylene, heteroalicyclylene, aralkylene, or (heteroalicyclyl)alkylene.

The term "amino" as used herein refers to a —$NH_2$ group.

The term "hydroxy" as used herein refers to a —OH group.

The term "cyano" group as used herein refers to a "—CN" group.

The term "azido" as used herein refers to a —$N_3$ group.

The term "thiol" as used herein refers to a —SH group.

The term "carboxylic acid" as used herein refers to —C(O)OH.

The term "thiocyanate" as used herein refers to —S—C≡N group.

The term "oxo-amine" as used herein refers to —O—$NH_2$ group, wherein one or more hydrogen of the —$NH_2$ can be optionally substituted by a R group. R can be independently hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate and phosphoramidate linkages. "Derivative", "analog" and "modified" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

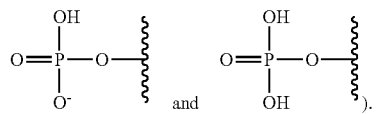

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Sometimes, "protecting group" and "blocking group" can be used interchangeably.

As used herein, the prefixes "photo" or "photo-" mean relating to light or electromagnetic radiation. The term can encompass all or part of the electromagnetic spectrum including, but not limited to, one or more of the ranges commonly known as the radio, microwave, infrared, visible, ultraviolet, X-ray or gamma ray parts of the spectrum. The part of the spectrum can be one that is blocked by a metal region of a surface such as those metals set forth herein. Alternatively or additionally, the part of the spectrum can be one that passes through an interstitial region of a surface such as a region made of glass, plastic, silica, or other material set forth herein. In particular embodiments, radiation can be used that is capable of passing through a metal. Alternatively or additionally, radiation can be used that is masked by glass, plastic, silica, or other material set forth herein.

As used herein, the term "phasing" refers to phenomena in SBS that is caused by incomplete removal of the 3' terminators and fluorophores, and failure to complete the incorporation of a portion of DNA strands within clusters by polymerases at a given sequencing cycle. Pre-phasing is caused by the incorporation of nucleotides without effective 3' terminators and the incorporation event goes 1 cycle ahead. Phasing and pre-phasing cause the extracted intensities for a specific cycle to consist of the signal of the current cycle as well as noise from the preceding and following cycles. As the number of cycles increases, the fraction of sequences per cluster affected by phasing increases, hampering the identification of the correct base. Pre-phasing can be caused by the presence of a trace amount of unprotected or unblocked 3'-OH nucleotides during sequencing by synthesis (SBS). The unprotected 3'-OH nucleotides could be generated during the manufacturing processes or possibly during the storage and reagent handling processes. Accordingly, the discovery of nucleotide analogues which decrease the incidence of pre-phasing is surprising and provides a great advantage in SBS applications over existing nucleotide analogues. For example, the nucleotide analogues provided can result in faster SBS cycle time, lower phasing and pre-phasing values, and longer sequencing read length.

3'-OH Protecting Groups —C(R)$_2$N$_3$

Some embodiments described herein relate to a modified nucleotide or nucleoside molecule having a removable 3'-hydroxy protecting group —C(R)$_2$N$_3$, wherein R is selected from the group consisting of hydrogen, —C(R$^1$)$_m$(R$^2$)$_n$, —C(=O)OR$^3$, —C(=O)NR$^4$R$^5$, —C(R$^6$)$_2$O(CH$_2$)$_p$NR$^7$R$^8$ and —C(R$^9$)$_2$O-Ph-C(=O)NR$^{10}$R$^{11}$, wherein R$^1$, R$^2$, R$^3$, R$^4$, R$^5$, R$^6$, R$^7$, R$^8$, R$^9$, R$^{10}$, R$^{11}$, m, n and p are defined above.

In some embodiments, one of R is hydrogen and the other R is —C(R$^1$)$_m$(R$^2$)$_n$. In some such embodiments, —C(R$^1$)$_m$(R$^2$)$_n$ is selected from —CHF$_2$, —CH$_2$F, —CHCl$_2$ or —CH$_2$Cl. In one embodiment, —C(R$^1$)$_m$(R$^2$)$_n$ is —CHF$_2$. In another embodiment, —C(R$^1$)$_m$(R$^2$)$_n$ is —CH$_2$F.

In some embodiments, one of R is hydrogen and the other R is —C(=O)OR$^3$. In some such embodiment, R$^3$ is hydrogen.

In some embodiments, one of R is hydrogen and the other R is —C(=O)NR$^4$R$^5$. In some such embodiments, both R$^4$ and R$^5$ are hydrogen. In some other such embodiments, R$^4$ is hydrogen and R$^5$ is C$_{1-6}$ alkyl. In still some other embodiments, both $R^4$ and $R^5$ are $C_{1-6}$ alkyl. In one embodiment, $R^5$ is n-butyl. In another embodiment, both $R^4$ and $R^5$ are methyl.

In some embodiments, one of R is hydrogen and the other R is $-C(R^6)_2O(CH_2)_pNR^7R^8$. In some such embodiments, both $R^6$ are hydrogen. In some such embodiments, both $R^7$ and $R^8$ are hydrogen. In some such embodiment, p is 0. In some other such embodiment, p is 6.

In some embodiments, one of R is hydrogen and the other R is $-C(R^9)_2O-Ph-C(=O)NR^{10}R^{11}$. In some such embodiments, both $R^9$ are hydrogen. In some such embodiments, both $R^{10}$ and $R^{11}$ are hydrogen. In some other such embodiments, $R^{10}$ is hydrogen and $R^{11}$ is a substituted alkyl. In one embodiment, $R^{11}$ is an amino substituted alkyl.

Deprotection of the 3'-OH Protecting Groups

In some embodiments, the 3'-OH protecting group is removed in a deprotecting reaction with a phosphine. The azido group in $-C(R)_2N_3$ can be converted to an amino group by contacting the modified nucleotide or nucleoside molecules with a phosphine. Alternatively, the azido group in $-C(R)_2N_3$ may be converted to an amino group by contacting such molecules with the thiols, in particular water-soluble thiols such as dithiothreitol (DTT). In one embodiment, the phosphine is tris(hydroxymethyl)phosphine (THP). Unless indicated otherwise, the reference to nucleotides is also intended to be applicable to nucleosides.

Detectable Labels

Some embodiments described herein relate to the use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3):951-960, 1999) discloses dansyl-functionalised fluorescent moieties that can be used in the present invention. Zhu et al. (*Cytometry* 28:206-211, 1997) describes the use of the fluorescent labels Cy3 and Cy5, which can also be used in the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11):4593-4602, 1987) and Smith et al. (*Nature* 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

Multiple labels can also be used in the present application, for example, bi-fluorophore FRET cassettes (*Tet. Let.* 46:8867-8871, 2000). Multi-fluor dendrimeric systems (*J. Am. Chem. Soc.* 123:8101-8108, 2001) can also be used. Although fluorescent labels are preferred, other forms of detectable labels will be apparent as useful to those of ordinary skill in the art. For example, microparticles, including quantum dots (Empodocles et al., *Nature* 399:126-130, 1999), gold nanoparticles (Reichert et al., *Anal. Chem.* 72:6025-6029, 2000) and microbeads (Lacoste et al., *Proc. Natl. Acad. Sci USA* 97(17):9461-9466, 2000) can all be used.

Multi-component labels can also be used in the present application. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

Unless indicated otherwise, the reference to nucleotides is also intended to be applicable to nucleosides. The present application will also be further described with reference to DNA, although the description will also be applicable to RNA, PNA, and other nucleic acids, unless otherwise indicated.

Linkers

In some embodiments described herein, the purine or pyrimidine base of the modified nucleotide or nucleoside molecules can be linked to a detectable label as described above. In some such embodiments, the linkers used are cleavable. The use of a cleavable linker ensures that the label can, if required, be removed after detection, avoiding any interfering signal with any labeled nucleotide or nucleoside incorporated subsequently.

In some other embodiments, the linkers used are non-cleavable. Since in each instance where a labeled nucleotide of the invention is incorporated, no nucleotides need to be subsequently incorporated and thus the label need not be removed from the nucleotide.

Those skilled in the art will be aware of the utility of dideoxynucleoside triphosphates in so-called Sanger sequencing methods, and related protocols (Sanger-type), which rely upon randomized chain-termination at a particular type of nucleotide. An example of a Sanger-type sequencing protocol is the BASS method described by Metzker.

Sanger and Sanger-type methods generally operate by the conducting of an experiment in which eight types of nucleotides are provided, four of which contain a 3'-OH group; and four of which omit the OH group and which are labeled differently from each other. The nucleotides used which omit the 3'-OH group-dideoxy nucleotides (ddNTPs). As known by one skilled in the art, since the ddNTPs are labeled differently, by determining the positions of the terminal nucleotides incorporated, and combining this information, the sequence of the target oligonucleotide may be determined.

The nucleotides of the present application, it will be recognized, may be of utility in Sanger methods and related protocols since the same effect achieved by using ddNTPs may be achieved by using the 3'-OH protecting groups described herein: both prevent incorporation of subsequent nucleotides.

Moreover, it will be appreciated that monitoring of the incorporation of 3'-OH protected nucleotides may be determined by use of radioactive $^{32}P$ in the phosphate groups attached. These may be present in either the ddNTPs themselves or in the primers used for extension.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidizing agents, light, temperature, enzymes etc. The linker as discussed herein may also be cleaved with the same catalyst used to cleave the 3'-O-protecting group bond. Suitable linkers can be adapted from standard chemical protecting groups, as disclosed in Greene & Wuts, Protective Groups in Organic Synthesis, John Wiley & Sons. Further suitable cleavable linkers used in solid-phase synthesis are disclosed in Guillier et al. (*Chem. Rev.* 100:2092-2157, 2000).

The use of the term "cleavable linker" is not meant to imply that the whole linker is required to be removed from, e.g., the nucleotide base. Where the detectable label is attached to the base, the nucleoside cleavage site can be located at a position on the linker that ensures that part of the linker remains attached to the nucleotide base after cleavage.

Where the detectable label is attached to the base, the linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytosine, thymidine or uracil and the N-4 position on cytosine.

A. Electrophilically Cleaved Linkers

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system.

The use of thiophilic metals, such as nickel, silver or mercury, in the cleavage of thioacetal or other sulfur-containing protecting groups can also be considered for the preparation of suitable linker molecules.

B. Nucleophilically Cleaved Linkers

Nucleophilic cleavage is also a well recognised method in the preparation of linker molecules. Groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

C. Photocleavable Linkers

Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenzyl compounds and nitroveratryl compounds. Linkers based on benzoin chemistry can also be used (Lee et al., *J. Org. Chem.* 64:3454-3460, 1999).

D. Cleavage under Reductive Conditions

There are many linkers known that are susceptible to reductive cleavage. Catalytic hydrogenation using palladium-based catalysts has been used to cleave benzyl and benzyloxycarbonyl groups. Disulfide bond reduction is also known in the art.

E. Cleavage under Oxidative Conditions

Oxidation-based approaches are well known in the art. These include oxidation of p-alkoxybenzyl groups and the oxidation of sulfur and selenium linkers. The use of aqueous iodine to cleave disulfides and other sulfur or selenium-based linkers is also within the scope of the invention.

F. Safety-Catch Linkers

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., J. Org. Chem. 62:5165-5168, 1997).

G. Cleavage by Elimination Mechanisms

Elimination reactions can also be used. For example, the base-catalysed elimination of groups such as Fmoc and cyanoethyl, and palladium-catalysed reductive elimination of allylic systems, can be used.

In some embodiments, the linker can comprise a spacer unit. The length of the linker is unimportant provided that the label is held a sufficient distance from the nucleotide so as not to interfere with any interaction between the nucleotide and an enzyme.

In some embodiments, the linker may consist of the similar functionality as the 3'-OH protecting group. This will make the deprotection and deprotecting process more efficient, as only a single treatment will be required to remove both the label and the protecting group. Particularly preferred linkers are phosphine-cleavable azide containing linkers.

Sequencing Methods

The modified nucleosides or nucleotides described herein can be used in conjunction with a variety of sequencing techniques. In some embodiments, the process to determine the nucleotide sequence of a target nucleic acid can be an automated process.

The nucleotide analogues presented herein can be used in a sequencing procedure, such as a sequencing-by-synthesis (SBS) technique. Briefly, SBS can be initiated by contacting the target nucleic acids with one or more labeled nucleotides, DNA polymerase, etc. Those features where a primer is extended using the target nucleic acid as template will incorporate a labeled nucleotide that can be detected. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with an array produced by the methods of the present disclosure are described, for example, in Bentley et al., *Nature* 456: 53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WIPO Pat. App. Ser. No. PCT/US11/57111, US Pat. App. Pub. No. 2005/0191698 A1, U.S. Pat. Nos. 7,595,883, and 7,244,559, each of which is incorporated herein by reference.

Sequencing-by-ligation reactions are also useful including, for example, those described in Shendure et al. *Science* 309:1728-1732 (2005); U.S. Pat. Nos. 5,599,675; and 5,750,341, each of which is incorporated herein by reference. Some embodiments can include sequencing-by-hybridization procedures as described, for example, in Bains et al., *Journal of Theoretical Biology* 135(3), 303-7 (1988); Drmanac et al., *Nature Biotechnology* 16, 54-58 (1998); Fodor et al., *Science* 251(4995), 767-773 (1995); and WO 1989/10977, each of which is incorporated herein by reference. In both sequencing-by-ligation and sequencing-by-hybridization procedures, nucleic acids that are present in gel-containing wells (or other concave features) are subjected to repeated cycles of oligonucleotide delivery and detection. Fluidic systems for SBS methods as set forth herein, or in references cited herei, can be readily adapted for delivery of reagents for sequencing-by-ligation or sequencing-by-hybridization procedures. Typically, the oligonucleotides are fluorescently labeled and can be detected using fluorescence detectors similar to those described with regard to SBS procedures herein or in references cited herein.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US Pat. App. Pub. Nos. 2009/0026082 A1; 2009/0127589 A1; 2010/0137143 A1; or 2010/0282617 A1, each of which is incorporated herein by reference.

EXAMPLES

Additional embodiments are disclosed in further detail in the following examples, which are not in any way intended to limit the scope of the claims. The synthesis of various modified nucleotide with protected 3'-hydroxy group are demonstrated in Examples 1-3.

Example 1

Synthesis of Nucleotides with 3'-OH Protecting Group

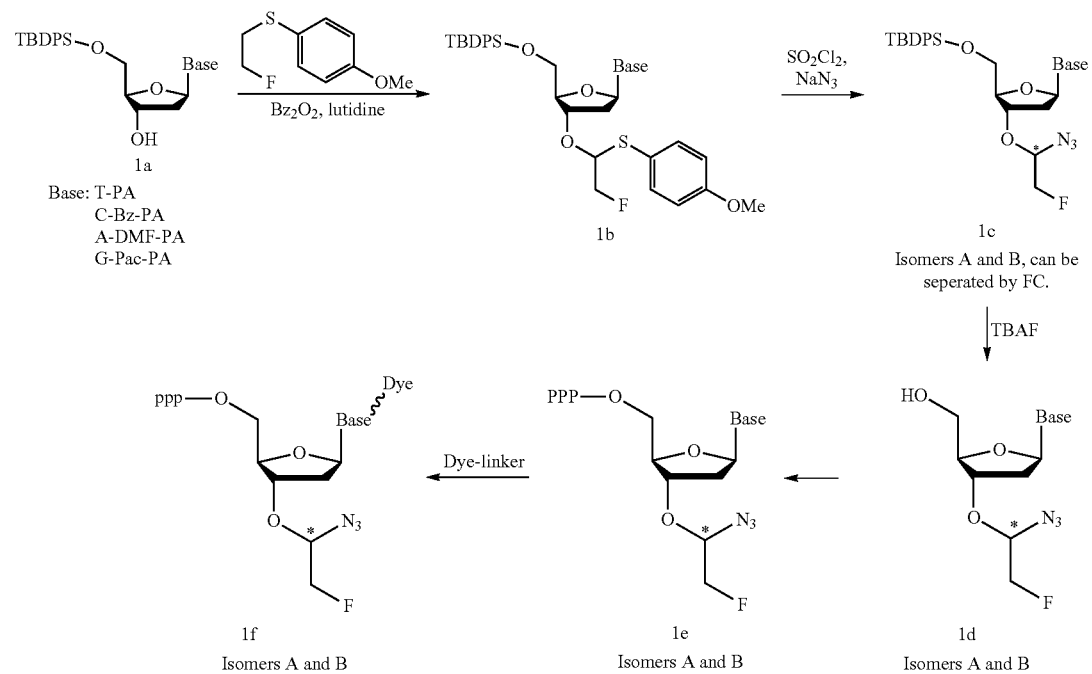

Scheme 1.

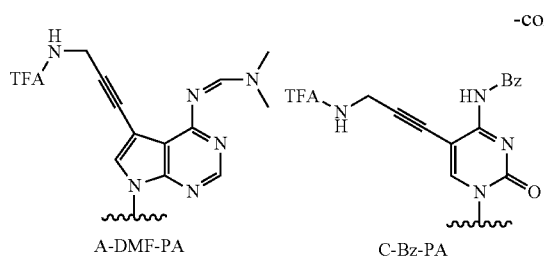 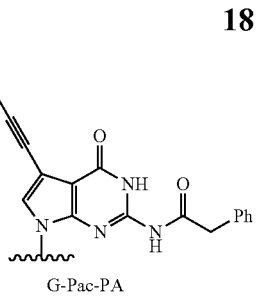

A-DMF-PA  C-Bz-PA  G-Pac-PA  T-PA

Scheme 1 illustrates a synthetic route for the preparation of the modified nucleotides with monofluoromethyl substituted azidomethyl as 3'-OH protecting groups. Compounds 1a-1f employ a modified thymine (T-PA) as the base. Other non-limiting examples of the bases that can be used include Cbz-PA, ADMF-PA, and GPac-PA, the structures of which are shown above in Scheme 1.

Experimental Procedures

To a solution of the starting nucleoside 1a (1.54 g, 2.5 mmol) in anhydrous $CH_3CN$ (25 ml) was added 2,6-lutidine (0.87 mL, 7.5 mmol), (2-fluoroethyl)(4-methoxyphenyl)sulfane (MPSF) (3.26 g, 17.5 mmol) and then $Bz_2O_2$ (50% pure, 8.47 g, 17.5 mmol) at 4° C. The reaction mixture was allowed to warm up slowly to room temperature. The mixture was stirred for other 6 hours. TLC monitored (EtOAc:DCM=2:8 v/v) to see complete consumption of the starting nucleoside. The reaction was then concentrated under reduced pressure to oily residue. To this mixture, petroleum ether (500 ml) was added and stirred vigorously for 10 min. The petroleum ether layer was decanted and the residue was repeated to treat with petroleum ether (×2). The oily residue was partitioned between $DCM/NaHCO_3$ (1:1) (300 mL). The organic layer was separated and the aqueous was further extracted into DCM (2×150 mL). Combined organic layers were dried over $MgSO_4$, filtered and the volatiles evaporated under reduced pressure. Crude product 1c was purified by Biotag silica gel column (50 g) using a gradient of petroleum ether to petroleum ether:EtOAc 1:1 (v/v) to afford 1.63 g nucleoside 1b as a pale yellow foam (diastereomers, 82% yield). $^1H$ NMR ($d_6$ DMSO, 400 MHz): δ, 0.95 (s, 9H, tBu), 2.16-2.28 (m, 2H, H-2'), 3.67 (s, OMe), 3.65-3.85 (m, 2H, HH-5'), 3.77 (dd, J=11.1, 4.5 Hz, 1H, HH-5'), 3.95-3.98 (m, 1H, H-4'), 4.04 (m, 2H, $CH_2F$), 4.63-4.64 (m, 1H, H-3'), 5.01-5.32 (s, 1H, CH), 6.00 (m, 1H, H-1'), 6.72-6.87 (m, 3H, Ar), 7.35-7.44 (m, 7H, Ar), 7.55-7.60 (m, 4H, Ar), 7.88 (s, 1H, H-6), 9.95 (brt, 1H, NH), 11.70 (s, 1H, NH).

To a solution of the starting nucleoside 1b (1.14 g, 1.4 mmol) in anhydrous $CH_2Cl_2$ (14 mL) with molecular sieve (4 Å) under $N_2$ was added cyclohexene (1.44 mL, 14 mmol). The mixture was cooled with a dry ice/acetone bath to −78° C. The solution of sulfuryl chloride (580 µL, 7.2 mmol) in DCM (14 ml) was slowly added over 90 minutes under $N_2$. After 20 mins at that temperature TLC (EtOAc:petroleum ether=1:1 v/v) indicated the full consumption of the starting nucleoside. Volatiles were evaporated under reduced pressure (and room temperature of 25° C.) and the oily residue was quickly subjected to high vacuum for a further 10 minutes until it foamed. The crude product was purged with $N_2$ and then dissolved in anhydrous DMF (5 mL) and $NaN_3$ (470 mg, 7 mmol) added at once. The resulting suspension was stirred at room temperature for 2 hours or until TLC indicated the completion of the reaction and formation of 1c as two isomer (a and b) The reaction mixture was partitioned between $EtOAc:NaHCO_3$ (1:1) (200 mL). The organic layer was separated and the aqueous was further extracted into EtOAc (2×100 mL). Combined organic extracts were dried over $MgSO_4$, filtered and the volatiles evaporated under reduced pressure. The two diastereoisomers of 1c (A and B) were separated by Biotag silica gel column (25 g) using a gradient of petroleum ether to petroleum ether:EtOAc 1:1 (v/v) as pale yellow foam.

Isomer A (370 mg, yield: 38%). $^1H$ NMR ($d_6$ DMSO, 400 MHz): δ 1.02 (s, 9H, tBu), 2.35-2.43 (m, 2H, H-2'), 3.76-3.80 (m, 1H, H-5'), 3.88-3.92 (m, 1H, H-5'), 4.10-4.12 (m, 1H, H-4'), 4.14 (d, J=4.1 Hz 2H, $NHCH_2$), 4.46-4.60 (m, 3H, H-3', CH2F), 5.05-5.09 (m, 1H, $CHN_3$), 6.11 (t, J=6.1 Hz, 1H, H-1'), 7.47-7.51 (m, 6H, Ar), 7.64-7.68 (m, 4H, Ar), 7.97 (s, 1H, H-6), 10.03 (bt, 1H, J=10.0 Hz, NH), 11.76 (s, 1H, NH). $^{19}F$ NMR: −74.3 ($CF_3$), −230.2 ($CH_2F$).

Isomer B (253 mg, yield:26%). $^1H$ NMR ($d_6$ DMSO, 400 MHz): δ 1.01 (s, 9H, tBu), 2.38-2.42 (m, 2H, H-2'), 3.74-3.78 (m, 1H, H-5'), 3.86-3.90 (m, 1H, H-5'), 4.00-4.05 (m, 1H, H-4'), 4.12 (d, J=4.1 Hz 2H, $NHCH_2$), 4.45-4.60 (m, 3H, H-3', CH2F), 5.00-5.14 (m, 1H, $CHN_3$), 6.09 (t, J=6.1 Hz, 1H, H-1'), 7.41-7.50 (m, 6H, Ar), 7.63-7.66 (m, 4H, Ar), 7.95 (s, 1H, H-6), 10.01 (bs, 1H, NH), 11.74 (s, 1H, NH). $^{19}F$ NMR: −74.5 (CF3), −230.4 (CH2F).

The starting material 1c (isomer A) (500 mg, 0.71 mmol) was dissolved in THF (3 mL) and cooled to 4° C. in ice-bath. Then TBAF (1.0 M in THF, 5 wt. % water, 1.07 mL, 1.07 mmol) was added slowly over a period of 5 mins. The reaction mixture was slowly warmed up to room temperature. Reaction progress was monitored by TLC (petroleum ether:EtOAc 3:7 (v/v)). The reaction was stopped after 1 hour when no more starting material was visible by TLC. The reaction solution was dissolved in EtOAc (50 mL) and added to $NaHCO_3$ (60 mL). The two layers were separated and the aqueous layer was extracted with additional DCM (50 mL×2). The organic extractions were combined, dried ($MgSO_4$), filtered, and evaporated to give a yellow oil. Crude product 1d (isomer A) was purified by Biotag silica gel column (10 g) using a gradient of petroleum ether: EtOAc 8:2 (v/v) to EtOAc as a white solid (183 mg, yield:56%).

Isomer A: $^1H$ NMR (400 MHz, $d_6$-DMSO): δ 2.24-2.35 (m, 2H, H-2'), 3.56-3.66 (m, 2H, H-5'), 3.96-4.00 (m, 1H, H-4'), 4.23 (s, 2H, $CH_2NH$), 4.33-4.37 (m, 1H, H-3'), 4.43-4.51 (m, CH2F), 5.12 (br.s, 1H, $CHN_3$), 5.23 (br.s, 1H, 5'-OH), 6.07 (t, J=6.7 Hz, 1H, H-1'), 8.26 (s, 1H, H-6), 10.11 (br s, 1H, NH), 11.72 (br s, 1H, NH). $^{19}F$ NMR: −74.3 (CF3), −230.5 (CH2F)

The same reaction was performed for 1c (isomer B) at 360 mg scale and afforded the corresponding product 1d (Isomer B, 150 mg, 63%). $^1H$ NMR (400 MHz, $d_6$-DMSO): δ 2.24-2.37 (m, 2H, H-2'), 3.57-3.70 (m, 2H, H-5'), 3.97-4.01 (m, 1H, H-4'), 4.23 (br.s, 2H, $CH_2NH$), 4.33-4.37 (m, 1H, H-3'), 4.44-4.53 (m, CH2F), 5.11-5.21 (br.s, 1H, $CHN_3$), 5.23 (br.s, 1H, 5'-OH), 6.07 (t, J=6.6 Hz, 1H, H-1'), 8.23 (s, 1H, H-6), 10.09 (br s, 1H, NH), 11.70 (br s, 1H, NH). $^{19}$F NMR: −74.1 (CF3), −230.1 (CH2F).

The preparation of the corresponding triphosphates 1e and the further attachment of dye to the nucleobase to afford the fully functional nucleoside triphosphate (ffN) 1f have been reported in WO 2004/018497 and are generally known by one skilled in the art.

Example 2

Synthesis of Nucleotides with 3'-OH Protecting Group

Experimental Procedures

To a solution of the starting nucleoside 2a (4.27 g, 6.9 mmol) in anhydrous CH$_3$CN (50 ml) was added 2,6-lutidine (2.4 mL, 20.7 mmol), S(CH$_2$CH$_2$OAc)$_2$ (12.2 g, 69 mmol) and then Bz$_2$O$_2$ (50% pure, 33.4 g, 69 mmol) at 4° C. The reaction mixture was allowed to warm up slowly to room temperature. The mixture was stirred for other 12 hours. TLC monitored (EtOAc:DCM=4:6 v/v) to see complete consumption of the starting nucleoside. The reaction was then concentrated under reduced pressure to an oily residue. To this mixture, petroleum ether (800 ml) was added and stirred vigorously for 10 min. The petroleum ether layer was decanted and the residue was repeatedly treated with petroleum ether (×2). The oily residue was then partitioned

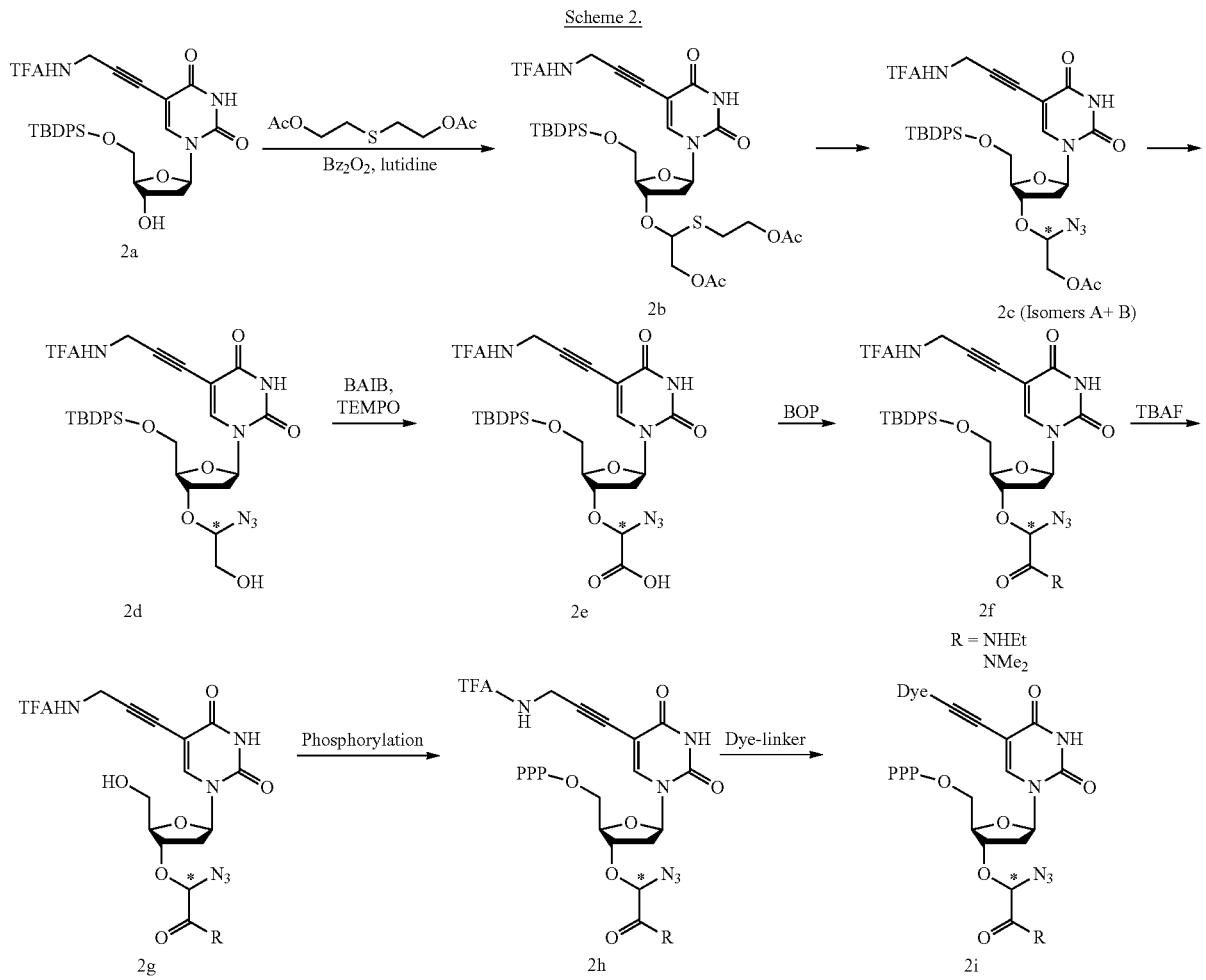

Scheme 2 illustrates a synthetic route for the preparation of the modified nucleotides with C-amido substituted azidomethyl as 3'-OH protecting groups. Compounds 2a-2i employ a modified thymine (T-PA) as the base. Other non-limiting examples of the bases that can be used include Cbz-PA, ADMF-PA, and GPac-PA, the structures of which are shown above in Scheme 1. In the experimental procedure, compound 2f with a N,N-dimethyl-C(=O)— substituted azidomethyl protecting group (R=NMe$_2$) and the subsequent reactions were reported. Compounds with other C-amido groups were also prepared, such as N-ethyl-C (=O)—(R=NHEt).

between DCM/NaHCO$_3$ (1:1) (1000 mL). The organic layer was separated and the aqueous layer was further extracted into DCM (2×500 mL). Combined organic layers were dried over MgSO$_4$, filtered and the volatiles evaporated under reduced pressure. Crude product 2b was purified by a Biotag silica gel column (100 g) using a gradient of petroleum ether to petroleum ether:EtOAc 2:8 (v/v) as a pale yellow foam (4.17 g, yield: 74%, diastereoisomers).

To a solution of the starting nucleoside 2b (4.54 g, 5.56 mmol) in anhydrous CH$_2$Cl$_2$ (56 mL) with molecular sieve (4 Å) under N$_2$ was added cyclohexene (5.62 mL, 56 mmol). The mixture was cooled with an ice bath to 4° C. The solution of sulfuryl chloride (1.13 mL, 13.9 mmol) in DCM (25 ml) was slowly added over 90 minutes under $N_2$. After 30 min at that temperature TLC (EtOAc:DCM=4:6 v/v) indicated 10% of the starting nucleoside 2b was left. Additional sulfuryl chloride (0.1 mL) was added into reaction mixture. TLC indicated complete conversion of 2b. Volatiles were evaporated under reduced pressure (and room temperature of 25° C.) and the oily residue was quickly subjected to a high vacuum for a further 10 minutes until it foamed. The crude product was purged with $N_2$ and then dissolved in anhydrous DMF (5 mL) and $NaN_3$ (1.8 g, 27.8 mmol) added at once. The resulting suspension was stirred at room temperature for 2 hours or until TLC indicated the completion of the reaction and formation of 2c as two isomers (A and B). The reaction mixture was partitioned between EtOAc:$NaHCO_3$ (1:1) (1000 mL). The organic layer was separated and the aqueous layer was further extracted into EtOAc (2×300 mL). Combined organic extracts were then dried over $MgSO_4$, filtered and the volatiles evaporated under reduced pressure. The two diastereoisomers 2c (isomer A and B) were separated by a Biotag silica gel column (100 g) using a gradient of petroleum ether to petroleum ether:EtOAc 1:1 (v/v) as pale yellow foam. Isomer A: 1.68 g, yield: 40.7%. Isomer B: 1.79 g, yield: 43.2%.

To a solution of the starting nucleoside 2c (isomer A) (1.63 g, 2.2 mmol) in MeOH/THF (1:1) (20 mL) was slowly added NaOH (1M in water) (2.2 mL, 2.2 mmol) and stirred in 4° C. The reaction progress was monitored by TLC (EtOAc:DCM=4:6 v/v). The reaction was stopped after 1 hour when no more starting material was visible by TLC. The reaction mixture was partitioned between DCM:$NaHCO_3$ (1:1) (150 mL). The organic layer was separated and the aqueous layer was further extracted into DCM (2×70 mL). Combined organic extracts were dried over $MgSO_4$, filtered and the volatiles evaporated under reduced pressure. The crude product 2d was purified by a Biotag silica gel column (10 g) using a gradient of petroleum ether:EtOAc (8:2) (v/v) to EtOAc as a pale yellow foam (1.1 g, yield: 71%).

The same reaction was repeated for 2c (isomer B, 1.57 g) and afforded the corresponding product 2d (isomer B, 1.01 g, 69% yield).

To a solution of the starting nucleoside 2d (isomer A) (700 mg, 1 mmol) in $CH_3CN$ (10 mL) was treated with TEMPO (63 mg, 0.4 mmol) and BAIB (644 mg, 2 mmol) at room temperature. The reaction progress was monitored by TLC (EtOAc:DCM=7:3 v/v). The reaction was stopped after 2 hour when no more starting material was visible by TLC. The reaction mixture was partitioned between DCM:$Na_2S_2O_3$ (1:1) (100 mL). The organic layer was separated and the aqueous layer was further extracted into DCM (2×70 mL). Combined organic extracts were then washed with NaCl (sat.). The organic layer was evaporated under reduced pressure without drying over $MgSO_4$ in order to prevent the product from precipitating out. The crude product 2e was purified by a Biotag silica gel column (10 g) using a gradient of petroleum ether:EtOAc (1:1) (v/v) to EtOAc to MeOH:EtOAc (1:9) as a pale yellow foam (isomer A, 482 mg, 68% yield).

The same reaction was performed for 2d (isomer B, 700 mg) and afforded the corresponding product 2e (isomer B, 488 mg, 69% yield).

To a solution of the starting nucleoside 2e (isomer A) (233 mg, 0.33 mmol) in $CH_3CN$ (10 mL) was added Hunig's base (173 µL, 1 mmol) and BOP (165 mg, 0.39 mmol) at room temperature. After stirring for 5 min, the solution was treated with Me2NH (2 M in THF) (0.41 ml, 0.82 mmol). The reaction progress was monitored by TLC (MeOH:DCM=1:9 v/v). The reaction was stopped after 2 hours when no more starting material was visible by TLC. The reaction mixture was partitioned between DCM:$NaHCO_3$ (1:1) (50 mL). The organic layer was separated and the aqueous layer was further extracted into DCM (2×30 mL). Combined organic extracts were dried over $MgSO_4$, filtered and the volatiles evaporated under reduced pressure. The crude product 2f (R=$NMe_2$) was purified by a Biotag silica gel column (10 g) using a gradient of DCM:EtOAc (8:2) (v/v) to EtOAc as a pale yellow foam (isomer A, 220 mg, 90% yield).

The same reaction was performed for 2e (isomer B, 249 mg) and afforded the corresponding product 2f (isomer B, 240 mg, 92% yield).

The starting material 2f (mixture of isomer A and B) (455 mg, 0.61 mmol) was dissolved in THF (2 mL) and cooled to 4° C. with ice-bath. Then, TBAF (1.0 M in THF, 5 wt. % water, 1.0 mL, 1.0 mmol) was added slowly over a period of 5 min. The reaction mixture was slowly warmed up to room temperature. The reaction progress was monitored by TLC (EtOAc). The reaction was stopped after 1 hour when no more starting material was visible by TLC. The reaction solution was dissolved in DCM (30 mL) and added to $NaHCO_3$ (30 mL). The two layers were separated and the aqueous layer was extracted with additional DCM (30 mL×2). The organic extractions were combined, dried ($MgSO_4$), filtered, and evaporated to give a yellow oil. Crude product 2g was purified by a Biotag silica gel column (10 g) using a gradient of DCM:EtOAc 8:2 (v/v) to EtOAc to MeOH:EtOAc (2:8) as a white solid (52% yield, 160 mg).

The preparation of the corresponding triphosphates 2h and the further attachment of dye to the nucleobase to afford the fully functional nucleoside triphosphate (ffN) 2i have been reported in WO 2004/018497 and are generally known by one skilled in the art.

Example 3

Synthesis of Nucleotides with 3'-OH Protecting Group

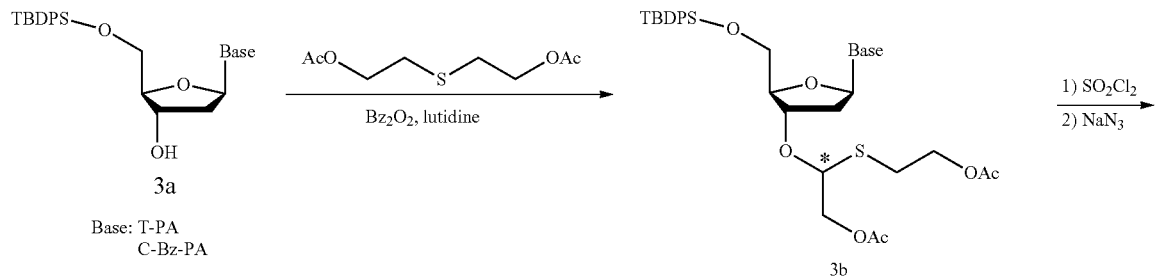

Scheme 3.

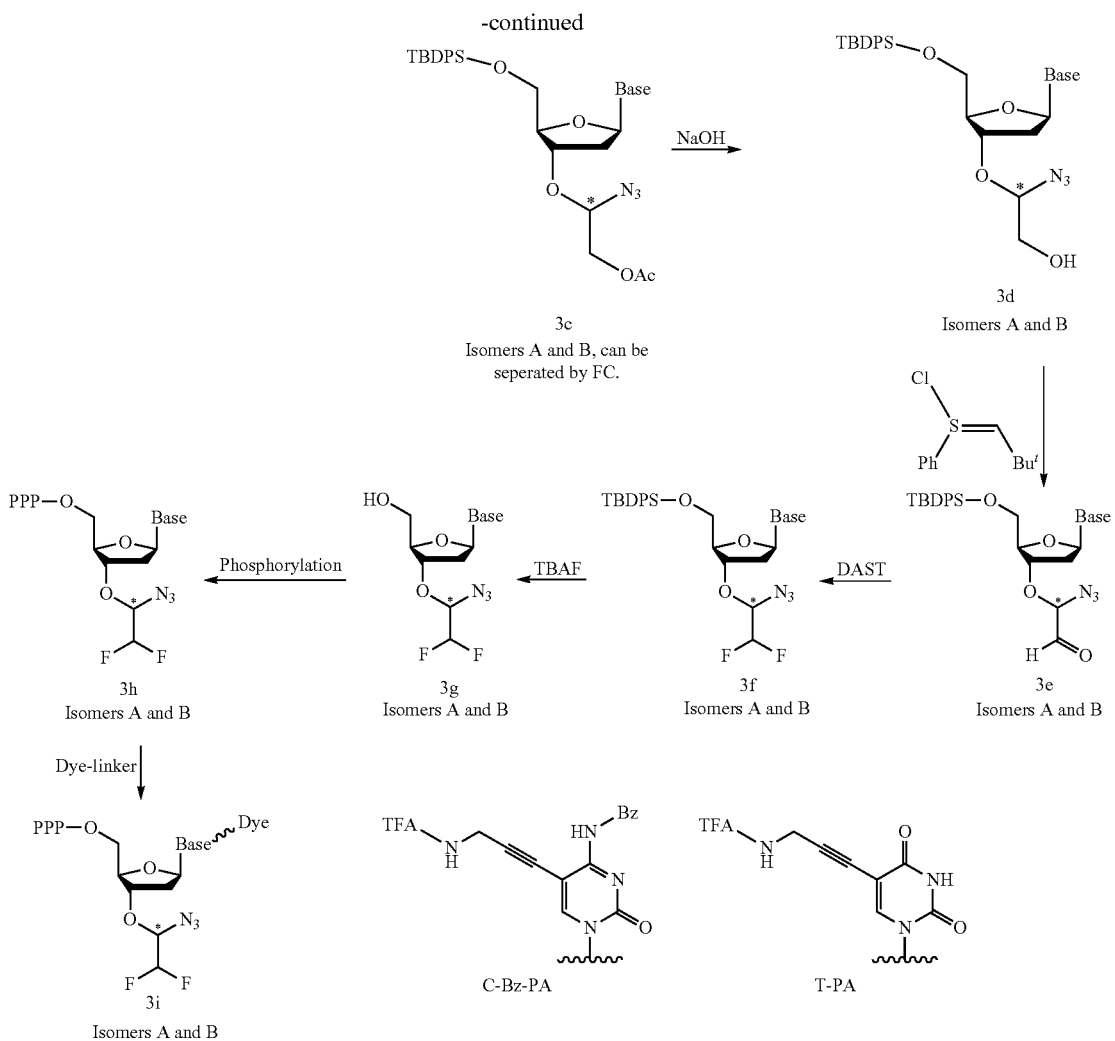

Scheme 3 illustrates a synthetic route for the preparation of modified nucleotides with difluoromethyl substituted azidomethyl 3'-OH protecting groups. Compounds 3a-3i employ a modified thymine (T-PA) as the base. Other non-limiting examples of the bases that can be used include Cbz-PA, ADMF-PA, and GPac-PA, the structures of which are shown above in Scheme 1. The procedure for the synthesis of 3b, 3c and 3d were described in Example 2.

Experimental Procedures

To a solution of the starting nucleoside 3d (isomer A) (490 mg, 0.7 mmol) and DBU (209 µL, 1.4 mmol) in anhydrous DCM (5 mL) was added slowly a solution of N-tert-butyl benzene sulfinimidoyl chloride (181 mg, 0.84 mmol) in anhydrous DCM (2 ml) at −78° C. The reaction mixture was stirred for 2 h at −78° C. The reaction progress was monitored by TLC (EtOAc:DCM 4:6 v/v). The reaction was stopped after 2 hours when there was still 10% starting material left by TLC, to prevent over-reacting. The reaction mixture was partitioned between DCM:NaHCO₃ (1:1) (50 mL). The aqueous layer was further extracted into DCM (2×30 mL). The organic extractions were combined, dried (MgSO₄), filtered, and evaporated to give a yellow oil. The crude product 3e was purified by a Biotag silica gel column (10 g) using a gradient of petroleum ether:EtOAc (8:2) (v/v) to petroleum ether:EtOAc (2:8) (v/v) as a pale yellow foam (isomer A, 250 mg, 51% yield).

The same reaction was performed for 3d (isomer B, 480 mg) and afforded the corresponding product 3e (isomer B, 240 mg, 50% yield).

To a solution of the starting nucleoside 3e (isomer A) (342 mg, 0.49 mmol), EtOH (15 µL, 0.25 mmol) in DCM (2.5 mL) was added slowly to the solution of DAST (181 mg, 0.84 mmol) in DCM (2.5 mL) at 4° C. (ice bath). The reaction mixture was stirred for 1 h at 4° C. The reaction progress was monitored by TLC (EtOAc:petroleum ether=3:7 v/v). The reaction was stopped after 1 hour. The reaction mixture was partitioned between DCM:NaHCO₃ (1:1) (50 mL). The aqueous layer was further extracted into DCM (2×30 mL). The organic extractions were combined, dried (MgSO₄), filtered, and evaporated to give a yellow oil. The crude product 3f was purified by a Biotag silica gel column (10 g) using a gradient of petroleum ether:EtOAc (9:1) (v/v) to petroleum ether:EtOAc (2:8) (v/v) as a pale yellow foam (isomer A, 100 mg, 28%).

The same reaction was performed for 3e (isomer B, 480 mg) and afforded the corresponding product 3f (isomer B, 240 mg, 50% yield).

The starting material 3f (isomer A) (124 mg, 0.17 mmol) was dissolved in THF (2 mL) and cooled to 4° C. with an ice bath. Then, TBAF (1.0 M in THF, 5 wt. % water, 255 µL, 10.255 mmol) was added slowly over a period of 5 min. The reaction mixture was slowly warmed up to room temperature. The reaction progress was monitored by TLC (EtOAc). The reaction was stopped after 1 hour when no more starting material was visible by TLC. The reaction solution was dissolved in DCM (30 mL) and added to NaHCO$_3$ (30 mL). The two layers were separated and the aqueous layer was extracted with additional DCM (30 mL×2). The organic extractions were combined, dried (MgSO$_4$), filtered, and evaporated to give a yellow oil. Crude product 3g was purified by a Biotag silica gel column (4 g) using a gradient of DCM:EtOAc 8:2 (v/v) to EtOAc to MeOH:EtOAc (2:8) as a pale yellow foam (isomer A, 54% yield, 44 mg).

Isomer A: $^1$H NMR (400 MtHz, d$_6$-DMSO): δ 2.24-2.35 (m, 2H, H-2'), 3.56-3.66 (m, 2H, H-5'), 3.96-4.00 (m, 1H, H-4'), 4.23 (s, 2H, CH$_2$NH), 4.33-4.37 (m, 1H, H-3'), 4.85 (s, 2H, OCH$_2$N$_3$), 5.23 (t, J=5.1 Hz, 1H, 5'-OH), 6.07 (t, J=6.7 Hz, 1H, H-1'), 8.19 (s, 1H, H-6), 10.09 (br s, 1H, NH), 11.70 (br s, 1H, NH). $^{19}$F NMR: −74.4 (CF3), −131.6 (CH2F).

The same reaction was performed for 3f (isomer B, 133 mg) and afforded the corresponding product 3g (isomer B, 48 mg, 54% yield). $^1$H NMR (400 MHz, d$_6$-DMSO): δ 2.27-2.44 (m, 2H, H-2'), 3.58-3.67 (m, 2H, H-5'), 4.00-4.02 (m, 1H, H-4'), 4.24 (d, J=4.1 Hz, 2H, CH$_2$NH), 4.57-4.58 (m, 1H, H-3'), 5.24-5.29 (m, 2H, 5'-OH, OCHN$_3$), 6.07-6.34 (m, 2H, H-1', CHF$_2$), 8.19 (s, 1H, H-6), 10.09 (br s, 1H, NH), 11.70 (br s, 1H, NH). $^{19}$F NMR: −74.2 (CF3), −131.4 (CH2F).

The preparation of the corresponding triphosphates 3h and the further attachment of dye to the nucleobase to afford the fully functional nucleotide (ffN) 3i have been reported in WO 2004/018497 and are generally known by one skilled in the art.

Example 4

Thermal Stability Testing of the 3'-OH Protecting Groups

Figure 1B:
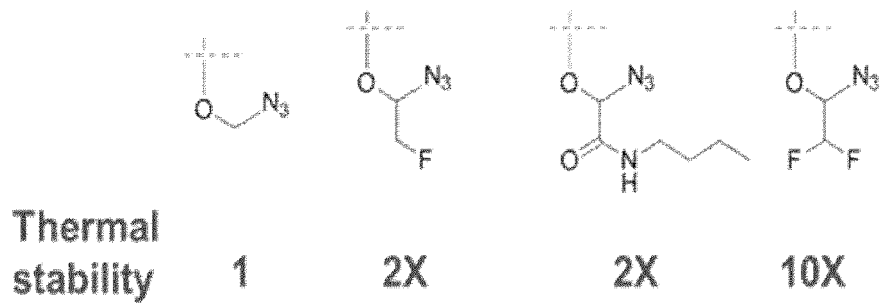
FIG. 1B illustrated the thermal stability of various 3'-OH protecting groups.

A variety of 3'-OH protecting groups were investigated in regard to their thermal stability (FIG. 1A). The thermal stability was evaluated by heating 0.1 mM of each 3'-OH protected nucleotide in a pH=9 buffer (tis-HCl 50 mM, NaCl 50 mM, tween 0.05%, Mg$_2$SO$_4$ 6 mM) at 60° C. Various times points were taken and HPLC was used to analyze the formation of un-blocked materials. The stabilities of —CH$_2$F and —C(O)NHBu were found to be about 2-fold greater than the standard azidomethyl (—CH$_2$N$_3$) protecting group. The stability of —CF$_2$H group was found to be about 10-fold greater than the standard (FIG. 1B).

Example 5

Deprotection of the 3'-OH Protecting Groups

Figures 2A, 2B:
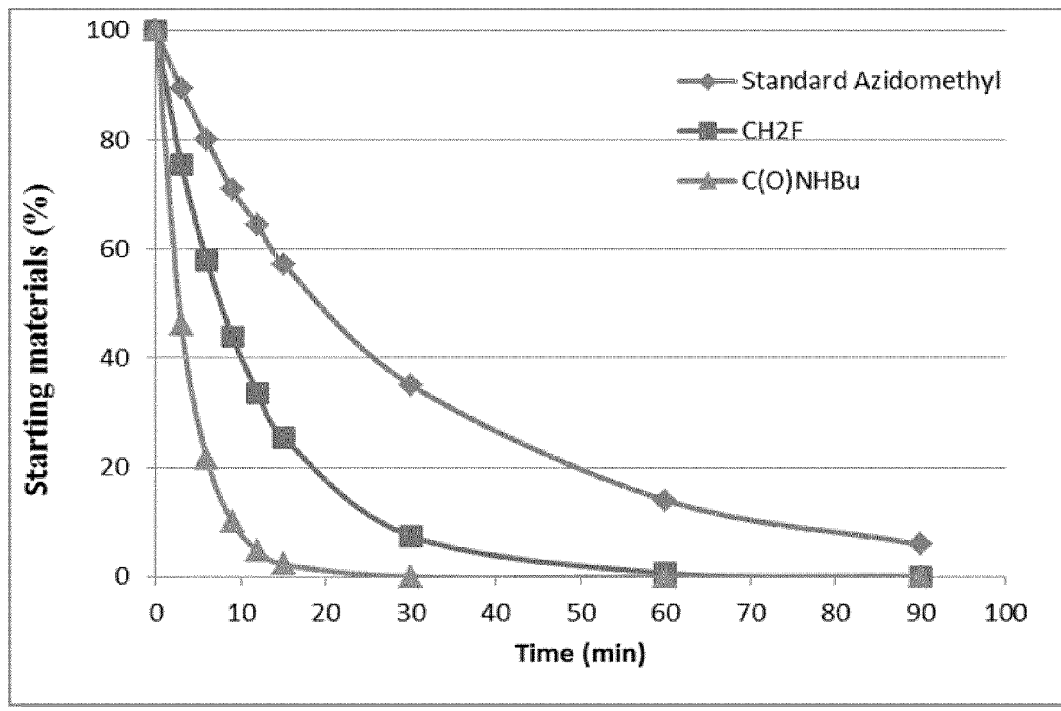
FIG. 2A illustrates the deprotection rate curve of three different 3'-OH protecting groups.
FIG. 2B shows a chart of the deprotection half time of three different 3'-OH protecting groups.

The deprotecting reaction rates of several 3'-OH protecting groups were also studied. The deprotection rate of the standard azidomethyl protecting group was compared with the —CH$_2$F substituted azidomethyl and —C(O)NHBu substituted azidomethyl. It was observed that both of the more thermally stable 3'-OH blocking groups were removed faster than the standard azidomethyl protecting group using phosphines (1 mM THP) as the deprotecting agent. See FIG. 2A. For example, the half-life of —CH$_2$F and —C(O)NHBu was 8.9 minutes and 2.9 minutes respectively, compared to the 20.4 minutes half-life of azidomethyl (FIG. 2B).

Example 6

Sequencing Test

Modified nucleotides with —CH$_2$F (mono-F) substituted azidomethyl 3'-OH protecting group were prepared and their sequencing performance was evaluated on Miseq platforms. It was envisaged that increased thermal stability of 3'-OH protecting groups would lead to a higher quality of nucleotides for sequencing chemistry with less contaminated 3'-unblocked nucleotides. The presence of 3'-unblocked nucleotides in the SBS-sequencing kits would therefore result in pre-phasing events, which were numerated as pre-phasing values.

Figure 3:
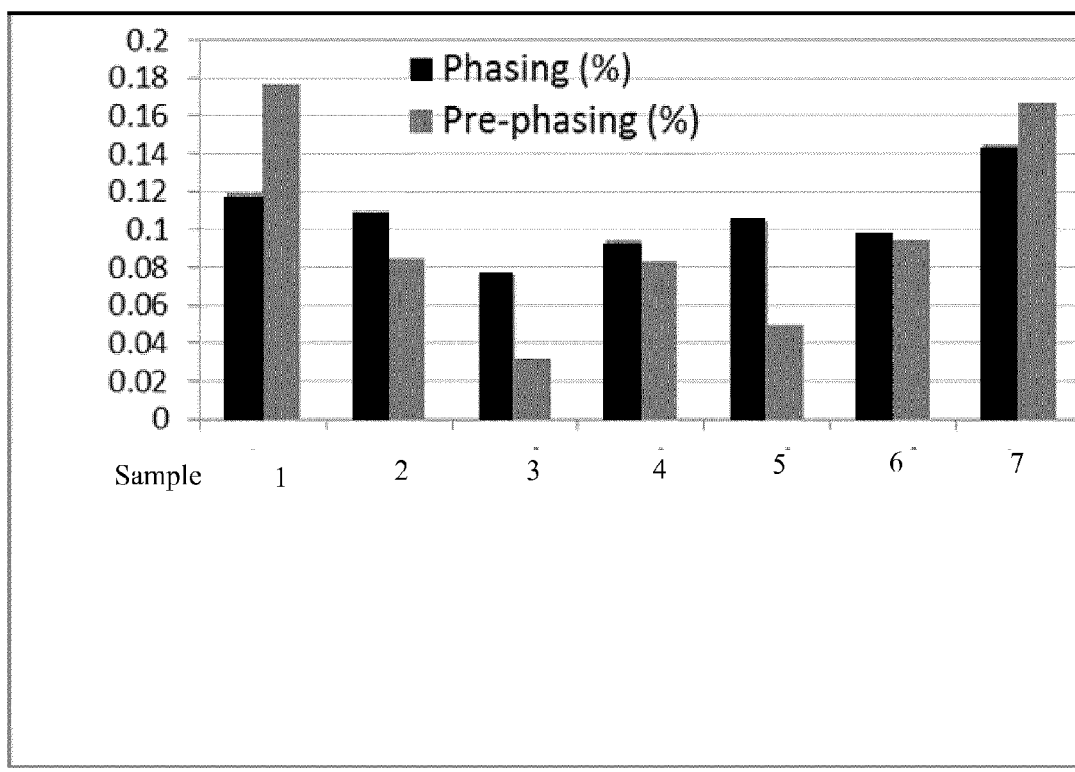
FIG. 3 shows the phasing and prephasing values of various modified nucleotide with a thermally stable 3'-OH protecting group in comparison and the standard protecting group.

Short 12-cycle sequencing experiments were first used to generate phasing and pre-phasing values. Mono-F substituted azidomethyl protected ffNs were used according to the following concentration: ffA-dye 1 (2 uM); ffT-dye 2 (10 uM), ffC-dye 3 (2 uM) and ffG-dye 4 (5 uM). Mono-F substituted azidomethyl group comprises both isomer A and B. Two dyes—dye 2 as in standard Miseq kits and dye 5 were used to label ffT. Table 1 shows various nucleotide combinations with A and B isomers of mono-F substituted azidomethyl that were evaluated in regard to phasing and pre-phasing impacts. In all cases, the pre-phasing values were substantially lower than the control that standard V2 Miseq kits nucleotides used (FIG. 3).

TABLE 1

| Sample | 3'-OH Protecting Group | Phasing (%) | Pre-phasing (%) |
|---|---|---|---|
| 1 | Std Miseq V2 IMX control | 0.119 | 0.177 |
| 2 | Mono-F-A-isomer | 0.11 | 0.085 |
| 3 | Mono-F-A isomer (ffT-Dye 5) | 0.076 | 0.032 |
| 4 | Mono-F-A isomer (A, C and G) + Mono-F-B-ffT-Dye 5 | 0.095 | 0.083 |
| 5 | Mono-F-A (G, ffT-Dye 5) and Mono-F-B (A, C) | 0.104 | 0.05 |
| 6 | Mono-F-A (G, T) and Mono-F-B (A, C) | 0.098 | 0.095 |
| 7 | Std Miseq V2 IMX control | 0.145 | 0.167 |

Sequencing Quality Testing

2×400 bp sequencing was carried out on Miseq to evaluate the potential of these nucleotides for sequencing quality improvement. The sequencing run was performed according to manufacturer's instructions (Illumina Inc., San Diego, Calif.). The standard incorporation buffer was replaced with an incorporation buffer containing all mono-F blocked FFNs, each with a separate dye label: ffA-dye 1 (2 uM), ffT-dye 2 (1 uM), ffC-dye 3 (2 uM) and ffG-dye 4 (5 uM). The DNA library used was made following the standard TruSeq HT protocol from *B cereus* genomic DNA.

Figure 4A:
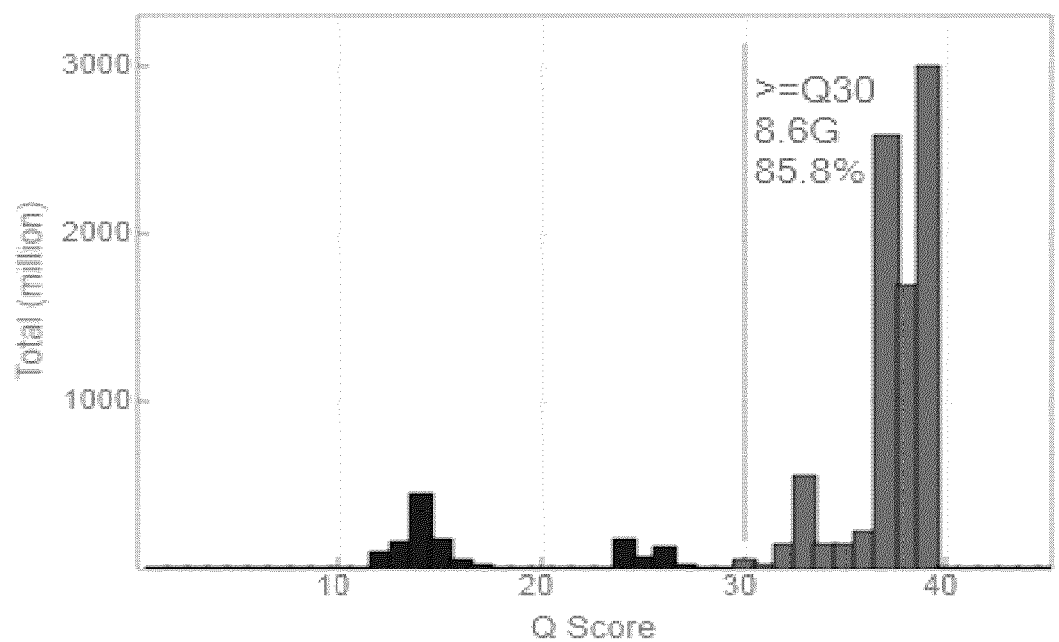
FIG. 4A shows the 2×400 bp sequencing data of mono-F ffNs-A-isomer in incorporation mix (IMX).
Figure 4B:
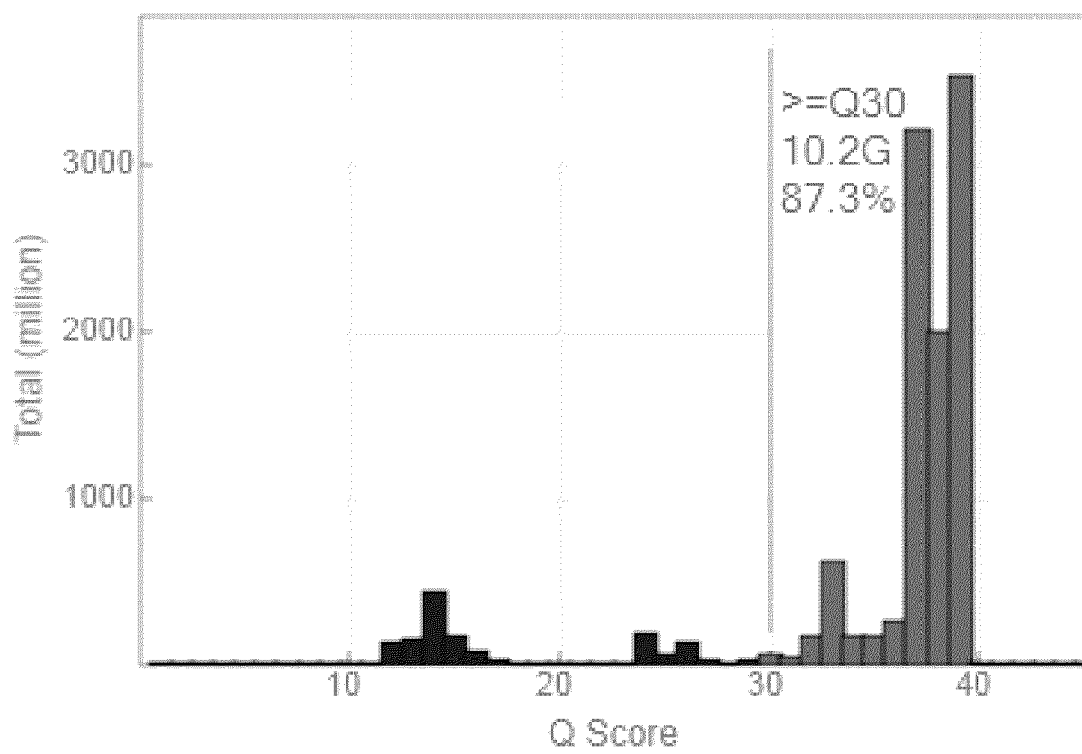
FIG. 4B shows the 2×400 bp sequencing data of mono-F ffNs-B-isomer in incorporation mix (IMX).

In both sequencing experiments (with mono-F block A and B isomer), very low pre-phasing values were observed. Coupled with low phasing values, application of these new nucleotides has generated superior 2×400 bp sequencing data with >80% of bases above Q30 in both cases (see FIG. 4A for the Q score of isomer A and FIG. 4B for the Q score chart of isomer B). These results demonstrate a great improvement compared with Miseq v2 kits (2×250 bp, 80% bases >Q30 in a typical R&D sequencing experiments, or 70% bases >Q30 as the stated specs). As shown below, Table 2 summarizes the sequencing data when using all mono-F ffNs-A-isomer in IMX. Table 3 summarizes the sequencing data using all mono-F ffNs-B-isomer in IMX.

TABLE 2

| Lane | Tiles | Density (K/mm2) | Clusters PF (%) | Phas/Pre phas (%) | Reads (M) | Reads PF (M) | % Mismatch Rate (PF) | % >= Q30 | Yield Total (G) |
|---|---|---|---|---|---|---|---|---|---|
| R1 | 28 | 690 +/− 14 | 93.1 +/− 0.7 | 0.075/0.051 | 13.35 | 12.43 | 0.58 ± 0.11 | 89.7 | 5 |
| R2 | 28 | 690 +/− 14 | 93.1 +/− 0.7 | 0.092/0.078 | 13.35 | 12.43 | 1.31 ± 0.25 | 81.9 | 5 |
| Total | | | | | | | | 85.8 | 9.9 |

TABLE 3

| Lane | Tiles | Density (K/mm2) | Clusters PF (%) | Phas/Pre phas (%) | Reads (M) | Reads PF (M) | % Mismatch Rate (PF) | % >= Q30 | Yield Total (G) |
|---|---|---|---|---|---|---|---|---|---|
| R1 | 28 | 816 +/− 9 | 92.7 +/− 0.6 | 0.073/0.033 | 15.79 | 14.64 | 0.44 ± 0.11 | 91.2 | 5.9 |
| R2 | 28 | 816 +/− 9 | 92.7 +/− 0.6 | 0.078/0.059 | 15.79 | 14.64 | 1.03 ± 0.19 | 83.4 | 5.9 |
| Total | | | | | | | | 87.3 | 11.7 |

What is claimed is:

1. A modified nucleotide or nucleoside molecule comprising a purine or pyrimidine base and a ribose or deoxyribose sugar moiety having a removable 3'-hydroxy protecting group forming a structure —O—C(R)$_2$N$_3$ covalently attached to the 3'-carbon atom, wherein R is independently selected from the group consisting of hydrogen, —C(R$^1$)$_m$(R$^2$)$_n$, —C(=O)OR$^3$, —C(=O)NR$^4$R$^5$, —C(R$^6$)$_2$O(CH$_2$)$_p$NR$^7$R$^8$ and —C(R$^9$)$_2$O-Ph-C(=O)NR$^{10}$R$^{11}$;

R$^1$ is selected from hydrogen, or optionally substituted alkyl;

R$^2$ is halogen;

R$^3$ is selected from hydrogen or optionally substituted alkyl;

each R$^4$ and R$^5$ is independently selected from hydrogen, optionally substituted alkyl, optionally substituted aryl, optionally substituted heteroaryl, or optionally substituted aralkyl;

each R$^6$ and R$^9$ is selected from hydrogen, optionally substituted alkyl or halogen;

each R$^7$, R$^8$, R$^{10}$ and R$^{11}$ is independently selected from hydrogen, optionally substituted alkyl, optionally substituted aryl, optionally substituted heteroaryl, or optionally substituted aralkyl;

m is an integer of 0 to 3;

n is an integer of 0 to 3; provided that the total of m+n equals to 3; and p is an integer of 0 to 6; provided that at least one R is not hydrogen.

2. The modified nucleotide or nucleoside molecule of claim 1, wherein one of R is hydrogen and the other R is —C(R$^1$)$_m$(R$^2$)$_n$.

3. The modified nucleotide or nucleoside molecule of claim 2, wherein —C(R$^1$)$_m$(R$^2$)$_n$ is selected from —CHF$_2$, —CH$_2$F, —CHCl$_2$ or —CH$_2$Cl.

4. The modified nucleotide or nucleoside molecule of claim 1, wherein one of R is hydrogen and the other R is —C(=O)OR$^3$.

5. The modified nucleotide or nucleoside molecule of claim 1, wherein one of R is hydrogen and the other R is —C(=O)NR$^4$R$^5$, and wherein R$^4$ is hydrogen and R$^5$ is C$_{1-6}$ alkyl.

6. The modified nucleotide or nucleoside molecule of claim 1, wherein one of R is hydrogen and the other R is —C(R$^6$)$_2$O(CH$_2$)$_p$NR$^7$R$^8$.

7. The modified nucleotide or nucleoside molecule of claim 6, wherein both R$^6$ are hydrogen.

8. The modified nucleotide or nucleoside molecule of claim 1, wherein one of R is hydrogen and the other R is —C(R$^9$)$_2$O-Ph-C(=O)NR$^{10}$R$^{11}$.

9. The modified nucleotide or nucleoside molecule of claim 8, wherein both R$^9$ are hydrogen, and wherein R$^{10}$ is hydrogen and R$^{11}$ is an amino substituted alkyl.

10. The modified nucleotide or nucleoside molecule of claim 1, wherein the 3'-hydroxy protecting group is removed in a deprotecting reaction with a phosphine.

11. The modified nucleotide or nucleoside molecule of claim 10, wherein the phosphine is tris(hydroxymethyl)phosphine (THP).

12. The modified nucleotide or nucleoside molecule of claim 1, wherein said base is linked to a detectable label via a cleavable linker.

13. The modified nucleotide or nucleoside molecule of claim 1, wherein said 3'-hydroxy protecting group is linked to a detectable label via a cleavable linker.

14. The modified nucleotide or nucleoside molecule of claim 13, wherein the detectable label is a fluorophore.

15. A method of preparing a growing polynucleotide complementary to a target single-stranded polynucleotide in a sequencing reaction, comprising incorporating a modified nucleotide molecule of claim 1 into the growing complementary polynucleotide, wherein the incorporation of the modified nucleotide prevents the introduction of any subsequent nucleotide into the growing complementary polynucleotide.

16. The method of claim 15, wherein the incorporation of the modified nucleotide molecule is accomplished by a terminal transferase, a terminal polymerase or a reverse transcriptase.

17. A method for determining the sequence of a target single-stranded polynucleotide, comprising
monitoring the sequential incorporation of complementary nucleotides, wherein at least one complementary nucleotide incorporated is a modified nucleotide molecule of claim 12; and
detecting the identity of the modified nucleotide molecule.

18. The method of claim 17, wherein the identity of the modified nucleotide is determined by detecting the detectable label linked to the base.

19. The method of claim 17, wherein the 3'-hydroxy protecting group and the detectable label are removed prior to introducing the next complementary nucleotide.

20. A kit comprising a plurality of modified nucleotide or nucleoside molecules of claim 1, and packaging materials therefor.

\* \* \* \* \*